(12) United States Patent
Nie et al.

(10) Patent No.: US 11,104,946 B2
(45) Date of Patent: Aug. 31, 2021

(54) DNA SEQUENCES RELATED TO DIAGNOSIS AND TREATMENT OF SYSTEMIC INFLAMMATORY RESPONSE SYNDROME

(71) Applicant: Inflammatix, Inc., Burlingame, CA (US)

(72) Inventors: Wensheng Nie, Belmont, CA (US); Timothy Sweeney, Redwood City, CA (US)

(73) Assignee: Inflammatix, Inc., Burlingame, CA (US)

( * ) Notice: Subject to any disclaimer, the term of this patent is extended or adjusted under 35 U.S.C. 154(b) by 323 days.

(21) Appl. No.: 16/410,161

(22) Filed: May 13, 2019

(65) Prior Publication Data

US 2020/0340036 A1 Oct. 29, 2020

Related U.S. Application Data

(60) Provisional application No. 62/837,433, filed on Apr. 23, 2019.

(51) Int. Cl.
| | | |
|---|---|---|
| *C12Q 1/68* | (2018.01) | |
| *C12Q 1/686* | (2018.01) | |
| *C12Q 1/6806* | (2018.01) | |
| *C12Q 1/6851* | (2018.01) | |
| *C12Q 1/6876* | (2018.01) | |

(52) U.S. Cl.
CPC ........... *C12Q 1/686* (2013.01); *C12Q 1/6806* (2013.01); *C12Q 1/6851* (2013.01); *C12Q 1/6876* (2013.01); *C12Q 2600/106* (2013.01); *C12Q 2600/112* (2013.01); *C12Q 2600/16* (2013.01)

(58) Field of Classification Search
CPC ...................................................... C12Q 1/68
USPC .................................................... 435/6.12
See application file for complete search history.

(56) References Cited

U.S. PATENT DOCUMENTS

| | | | |
|---|---|---|---|
| 6,653,131 B2 | 11/2003 | Humes | |
| 2009/0203534 A1* | 8/2009 | Hossain | C12Q 1/6883 506/9 |
| 2011/0076685 A1 | 3/2011 | Moeller et al. | |
| 2014/0037649 A1 | 2/2014 | Brandon et al. | |
| 2016/0312286 A1 | 10/2016 | Brandon et al. | |
| 2017/0235871 A1 | 8/2017 | Eden et al. | |
| 2018/0291449 A1 | 10/2018 | Khatri et al. | |

FOREIGN PATENT DOCUMENTS

| | | | | |
|---|---|---|---|---|
| WO | WO-2017214061 A1 * | 12/2017 | ............. | G01N 33/53 |
| WO | 2018060739 A2 | 4/2018 | | |

OTHER PUBLICATIONS

Application No. PCT/US2020/029150, International Search Report and Written Opinion, dated Sep. 29, 2020, 15 pages.

* cited by examiner

*Primary Examiner* — Aaron A Priest

(74) *Attorney, Agent, or Firm* — Kilpatrick Townsend & Stockton LLP

(57) ABSTRACT

This invention provides triple primer and probe combinations that function efficiently in PCR-based amplification systems using undigested genomic DNA and are useful for the diagnosis and subsequent treatment of systemic inflammatory disease.

16 Claims, 2 Drawing Sheets
Specification includes a Sequence Listing.

SEQUENCE LISTING

<160> NUMBER OF SEQ ID NOS: 45

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agtcactggg agcaactg                                                   18

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
accaagttca tcctgggctc catt                                            24

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caatgacagc cgcaatgg                                                   18

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agtgaccagt gtggccaaag t                                               21

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
cctctggctc tgccgtagtt ttgcc                                           25

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tccaatcaca actgtagcaa tcct                                            24

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
agtgaccagt gtggccaaag t                                    21

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic probe

<400> SEQUENCE: 8
aggggcaaaa ctacggcaga gccag                                25

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
tccaatcaca actgtagcaa tcct                                 24

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
agtgaccagt gtggccaaag t                                    21

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic probe

<400> SEQUENCE: 11
aggggcaaaa ctacggcaga gcca                                 24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
tccaatcaca actgtagcaa tcct                                 24

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccctcatttc ctggaccaaa                                                    20

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
ctgctgagag atgccattcg gagg                                               24

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aaccacgtcg atgttgtagg                                                    20

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgctgagaga tgccattcg                                                     19

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
atcgacgtgg ttgctgtggt gaa                                                23

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctacaactag cccaacctca c                                                  21

```
<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tttaggtgca gtggtgtgg                                                    19

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
cctccgaatg gcatctctca gcag                                              24

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtgcccactg tgtcgtt                                                      17

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tccaaggtgc acaagaatga                                                   20

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
attctgcaga ccctgtgtga gcag                                              24

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcagagcctc gttctccctt                                                   19
```

```
<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tccaaggtgc acaagaatga                                              20

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
tgtgagcagc ttcggaagga gaac                                         24

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atccaacttg gccttcagag                                              20

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ggagtatgcg cattttcagt actg                                         24

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
agagcccgga gcatgtgccc tc                                           22

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gcatggatgt gggctgtatg                                              20
```

```
<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggagtatgcg cattttcagt actg                                          24

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
cccggagcat gtgccctccc                                               20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gcatggatgt gggctgtatg                                               20

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggagtatgcg cattttcagt actg                                          24

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
ccggagcatg tgccctccca                                               20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gcatggatgt gggctgtatg                                               20
```

```
<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggagtatgcg cattttcagt actg                                           24

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
agcatgtgcc ctcccaagca gg                                             22

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gcatggatgt gggctgtatg                                                20

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tcctggtcct tggtctcaa                                                 19

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
ctgcatccac agttccagag cct                                            23

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42 tgatgggga agggtac                                                    18
```

```
<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
acttctacaa cgtggacatg ag                                              22

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
aggctatgtg gtaccttcct gggt                                            24

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggtcctcggt aaacataact ctc                                             23
```

DNA SEQUENCES RELATED TO DIAGNOSIS AND TREATMENT OF SYSTEMIC INFLAMMATORY RESPONSE SYNDROME

CROSS-REFERENCES TO RELATED APPLICATIONS

This application claims priority to U.S. Provisional Application No. 62/837,433, filed Apr. 23, 2019, the disclosure of which is hereby incorporated by reference in its entirety for all purposes.

REFERENCE TO A "SEQUENCE LISTING," A TABLE, OR A COMPUTER PROGRAM LISTING APPENDIX SUBMITTED ON A COMPACT DISK

This application includes a Sequence Listing as a text file named "103604-1138699-000210US_SL.txt" created May 8, 2019, and containing 10,458 bytes. The material contained in this text file is incorporated by reference in its entirety for all purposes.

FIELD OF THE INVENTION

This invention provides triple primer and probe combinations that function efficiently in PCR-based amplification systems in the presence of undigested genomic DNA and are useful for the diagnosis and subsequent treatment of systemic inflammatory disease.

BACKGROUND OF THE INVENTION

SIRS, or Systemic Inflammatory Response Syndrome, refers to a set of clinical features resulting from an immune response to an acute insult such as infection, trauma, burns, ischemia, or surgery. SIRS can include features such as fever, elevated heart or respiratory rate, or abnormal white blood cell count. Because of the complex etiology of SIRS, and because of the potential clinical severity of its various causes and the frequent need to introduce rapid appropriate therapy, e.g., antibiotics in the case of infection, it is critical to develop new methods for rapidly diagnosing SIRS in patients and identifying the nature and severity of its underlying cause.

One potential cause of SIRS is infection. Early and accurate diagnosis of infection is key to improving patient outcomes and reducing antibiotic resistance. The mortality rate of bacterial infection, for example, increases by 8% for each hour by which antibiotics are delayed.

At the same time, indiscriminate prescription of antibiotics to patients without bacterial infections increases rates of morbidity and antimicrobial resistance. Unfortunately, it can be difficult to distinguish patients with noninfectious inflammation from those with bacterial and viral infections, and the rate of inappropriate antibiotic prescriptions in the hospital setting is estimated at 30% to 50%.

There is currently no gold standard point-of-care diagnostic that can broadly determine the presence and type of infection. Current microbiological offerings generally rely on direct pathogen detection, which is limited by insufficient accuracy. Further, although polymerase chain reaction (PCR)-based molecular diagnostics can profile pathogens directly from a blood culture, such methods rely on the presence of adequate numbers of pathogens in the blood. Moreover, they are limited to detecting a discrete range of pathogens.

Accordingly, there is a growing need for molecular diagnostics that profile the host gene response. A number of biomarkers have been identified, for example, that can help distinguish from among patients with SIRS those that have non-infectious, bacterial, or viral sources of inflammation. The levels of such biomarkers can be assessed, for example, through amplification-based assays that measure their relative expression levels in blood cells from patients. Given the importance of extremely rapid diagnoses for patients with SIRS in order to enable decisions regarding an appropriate course of action, early, accurate and rapid differentiation between viral and bacterial infections is critical to guide the choice of antimicrobial treatment, improve patient outcome, and ensure antimicrobial stewardship. The present invention addresses these and other needs.

BRIEF SUMMARY OF THE INVENTION

The present invention is based upon the surprising discovery that certain combinations of primer pairs and probes can be effectively used in quantitative real-time RNA-based amplification assays, e.g., in TaqMan qRT-PCR assays, in multiplex, without being affected by the presence of genomic DNA.

In one aspect, the present disclosure provides a method of treating systemic inflammatory response syndrome (SIRS), comprising the steps of: a) selecting a patient presenting clinical symptoms of systemic inflammatory response syndrome [SIRS] and having a biomarker gene score exceeding a threshold value indicating that the patient has a likelihood ratio of 2 or greater for the presence of a bacterial or of a viral infection compared to a reference population, wherein the score is based on the measured expression levels in blood from the patient of at least two biomarker genes selected from the group consisting of IFI27, GPAA1, HK3, TNIP1, and LAX1; (i) where the expression levels of the biomarker genes, e.g., absolute expression levels or relative expression levels as compared to control, e.g., housekeeping, genes, are quantitatively determined by amplification and detection of a subsequence of mRNA encoding the biomarker genes, (ii) where the amplification and detection arises from the use of amplification primer pairs in the presence of undigested genomic DNA and fluorescent probes that bind to the amplified biomarker gene subsequences, and (iii) where the primer pairs and probes used to amplify the biomarker genes are selected from the group of primer and probe triplet member combinations consisting of AGTCACTGG-GAGCAACTG (SEQ ID NO: 1), ACCAAGTT-CATCCTGGGCTCCATT (SEQ ID NO: 2), and CAATGACAGCCGCAATGG (SEQ ID NO: 3) (triplet IFI27-B); AGTGACCAGTGTGGCCAAAGT (SEQ ID NO: 4), CCTCTGGCTCTGCCGTAGTTTTGCC (SEQ ID NO: 5), and TCCAATCACAACTGTAGCAATCCT (SEQ ID NO: 6) (triplet IFI127-3AA); AGTGACCAGTGTGGC-CAAAGT (SEQ ID NO: 7), AGGGGCAAAAC-TACGGCAGAGCCAG (SEQ ID NO: 8), and TCCAAT-CACAACTGTAGCAATCCT (SEQ ID NO: 9) (triplet IFI27-3C); AGTGACCAGTGTGGCCAAAGT (SEQ ID NO: 10), AGGGGCAAAACTACGGCAGAGCCA (SEQ ID NO: 11), and TCCAATCACAACTGTAGCAATCCT (SEQ ID NO: 12) (triplet IFI27-3D); CCCTCAT-TTCCTGGACCAAA (SEQ ID NO: 13), CTGCT-GAGAGATGCCATTCGGAGG (SEQ ID NO: 14), and AACCACGTCGATGTTGTAGG (SEQ ID NO: 15) (triplet HK3-A); TGCTGAGAGATGCCATTCG (SEQ ID NO: 16), ATCGACGTGGTTGCTGTGGTGAA (SEQ ID NO: 17), and CTACAACTAGCCCAACCTCAC (SEQ ID NO: 18)

(triplet HK3-B); TTTAGGTGCAGTGGTGTGG (SEQ ID NO: 19), CCTCCGAATGGCATCTCTCAGCAG (SEQ ID NO: 20), and GTGCCCACTGTGTCGTT (SEQ ID NO: 21) (triplet HK3-C-NEW); TCCAAGGTGCACAAGAATGA (SEQ ID NO: 22), ATTCTGCAGACCCTGTGTGAGCAG (SEQ ID NO: 23), and TCAGAGCCTCGTTCTCCTT (SEQ ID NO: 24) (triplet TNIP1-A); TCCAAGGTGCACAAGAATGA (SEQ ID NO: 25), TGTGAGCAGCTTCGGAAGGAGAAC (SEQ ID NO: 26), and ATCCAACTTGGCCTTCAGAG (SEQ ID NO: 27) (triplet TNIP-C); GGAGTATGCGCATTTTCAGTACTG (SEQ ID NO: 28), AGAGCCCGGAGCATGTGCCCTC (SEQ ID NO: 29), and GCATGGATGTGGGCTGTATG (SEQ ID NO: 30) (triplet LAX1-D); GGAGTATGCGCATTTTCAGTACTG (SEQ ID NO: 31), CCCGGAGCATGTGCCCTCCC (SEQ ID NO: 32), and GCATGGATGTGGGCTGTATG (SEQ ID NO: 33) (triplet LAX1-E); GGAGTATGCGCATTTTCAGTACTG (SEQ ID NO: 34), CCGGAGCATGTGCCCTCCCA (SEQ ID NO: 35), and GCATGGATGTGGGCTGTATG (SEQ ID NO: 36) (triplet LAX1-F); GGAGTATGCGCATTTTCAGTACTG (SEQ ID NO: 37), AGCATGTGCCCTCCCAAGCAGG (SEQ ID NO: 38), and GCATGGATGTGGGCTGTATG (SEQ ID NO: 39) (triplet LAX1-G); TCCTGGTCCTTGGTCTCAA (SEQ ID NO: 40), CTGCATCCACAGTTCCAGAGCCT (SEQ ID NO: 41), and TGATGGGGGAAGGGGTAC (SEQ ID NO: 42) (triplet GPAA1-WN-Y), including variants of the combination triplet members, wherein the variants of the members comprise 95% or greater sequence identity to these sequences and the primer and probe variants have a GC content of between 45 and 65%; and, b) treating the selected patient with an antimicrobial agent in an amount sufficient to reduce the clinical symptoms of SIRS.

In one embodiment, the antimicrobial agent is an antiviral agent. In another embodiment, the antimicrobial agent is an antibacterial agent. In one embodiment, one of the biomarker genes is GPAA1 or IF127. In one embodiment, the score is further based on the expression level of the biomarker gene CTSB, wherein the CTSB biomarker gene is detected by a combination of three DNA sequences consisting of a forward primer, a reverse primer, and a fluorescent probe having the sequences ACTTCTACAACGTGGACATGAG (SEQ ID NO: 43), AGGCTATGTGGTACCTTCCTGGGT (SEQ ID NO: 44), and GGTCCTCGGTAAACATAACTCTC (SEQ ID NO: 45), and. In one embodiment, the probes are labeled with a fluorophore having a maximum fluorescent emission of between 400 and 600 nm.

In another aspect, the present disclosure provides a genetic amplification system for diagnosing systemic inflammatory response syndrome [SIRS], comprising a multiplicity of reaction vessels and a blood sample from a patient presenting clinical symptoms of SIRS, wherein the system can detect the expression levels of at least two biomarker genes whose measured levels can be used to generate a score indicative of the likelihood of the presence of a bacterial or a viral infection in the patient, wherein the biomarker genes are selected from the group consisting of IFI27, GPAA1, HK3, TNIP1, and LAX1; (i) where the levels of the biomarker genes, e.g., absolute expression levels or relative expression levels as compared to control, e.g., housekeeping, genes, are quantitatively determined by amplification and detection of a subsequence of mRNA encoding the biomarker genes, (ii) where the amplification and detection arises from the use of amplification primer pairs in the presence of undigested genomic DNA and fluorescent probes that bind to the amplified biomarker gene subsequence, and (iii) where the primer pairs and probes used to amplify the biomarker genes are selected from the group of primer and probe triplet member combinations consisting of AGTCACTGGGAGCAACTG (SEQ ID NO: 1), ACCAAGTTCATCCTGGGCTCCATT (SEQ ID NO: 2), and CAATGACAGCCGCAATGG (SEQ ID NO: 3) (triplet IFI27-B); AGTGACCAGTGTGGCCAAAGT (SEQ ID NO: 4), CCTCTGGCTCTGCCGTAGTTTTGCC (SEQ ID NO: 5), and TCCAATCACAACTGTAGCAATCCT (SEQ ID NO: 6) (triplet IFI127-3AA); AGTGACCAGTGTGGCCAAAGT (SEQ ID NO: 7), AGGGGCAAAACTACGGCAGAGCCAG (SEQ ID NO: 8), and TCCAATCACAACTGTAGCAATCCT (SEQ ID NO: 9) (triplet IFI27-3C); AGTGACCAGTGTGGCCAAAGT (SEQ ID NO: 10), AGGGGCAAAACTACGGCAGAGCCA (SEQ ID NO: 11), and TCCAATCACAACTGTAGCAATCCT (SEQ ID NO: 12) (triplet IFI27-3D); CCCTCATTTCCTGGACCAAA (SEQ ID NO: 13), CTGCTGAGAGATGCCATTCGGAGG (SEQ ID NO: 14), and AACCACGTCGATGTTGTAGG (SEQ ID NO: 15) (triplet HK3-A); TGCTGAGAGATGCCATTCG (SEQ ID NO: 16), ATCGACGTGGTTGCTGTGGTGAA (SEQ ID NO: 17), and CTACAACTAGCCCAACCTCAC (SEQ ID NO: 18) (triplet HK3-B); TTTAGGTGCAGTGGTGTGG (SEQ ID NO: 19), CCTCCGAATGGCATCTCTCAGCAG (SEQ ID NO: 20), and GTGCCCACTGTGTCGTT (SEQ ID NO: 21) (triplet HK3-C-NEW); TCCAAGGTGCACAAGAATGA (SEQ ID NO: 22), ATTCTGCAGACCCTGTGTGAGCAG (SEQ ID NO: 23), and TCAGAGCCTCGTTCTCCTT (SEQ ID NO: 24) (triplet TNIP1-A); TCCAAGGTGCACAAGAATGA (SEQ ID NO: 25), TGTGAGCAGCTTCGGAAGGAGAAC (SEQ ID NO: 26), and ATCCAACTTGGCCTTCAGAG (SEQ ID NO: 27) (triplet TNIP-C); GGAGTATGCGCATTTTCAGTACTG (SEQ ID NO: 28), AGAGCCCGGAGCATGTGCCCTC (SEQ ID NO: 29), and GCATGGATGTGGGCTGTATG (SEQ ID NO: 30) (triplet LAX1-D); GGAGTATGCGCATTTTCAGTACTG (SEQ ID NO: 31), CCCGGAGCATGTGCCCTCCC (SEQ ID NO: 32), and GCATGGATGTGGGCTGTATG (SEQ ID NO: 33) (triplet LAX1-E); GGAGTATGCGCATTTTCAGTACTG (SEQ ID NO: 34), CCGGAGCATGTGCCCTCCCA (SEQ ID NO: 35), and GCATGGATGTGGGCTGTATG (SEQ ID NO: 36) (triplet LAX1-F); GGAGTATGCGCATTTTCAGTACTG (SEQ ID NO: 37), AGCATGTGCCCTCCCAAGCAGG (SEQ ID NO: 38), and GCATGGATGTGGGCTGTATG (SEQ ID NO: 39) (triplet LAX1-G); TCCTGGTCCTTGGTCTCAA (SEQ ID NO: 40), CTGCATCCACAGTTCCAGAGCCT (SEQ ID NO: 41), and TGATGGGGGAAGGGGTAC (SEQ ID NO: 42) (triplet GPAA1-WN-Y), including variants of the combination triplet members wherein the variants of the members comprise 95% or greater sequence identity to these sequences and the primer and probe variants have a GC content of between 45 and 65%.

In one embodiment, the reaction vessels are in a thermocycling device designed to heat and cool the vessels. In one embodiment, one of the biomarker genes is GPAA1 or IF127. In one embodiment, the system can further detect the level of the CTSB biomarker gene in the patient, wherein the CTSB biomarker gene is detected by a combination of three DNA sequences consisting of a forward primer, a reverse primer, and a fluorescent probe having the sequences ACTTCTACAACGTGGACATGAG (SEQ ID NO: 43), AGGCTATGTGGTACCTTCCTGGGT (SEQ ID NO: 44), and GGTCCTCGGTAAACATAACTCTC (SEQ ID NO: 45).

In one embodiment, the probes are labeled with a fluorophore having a maximum fluorescent emission of between 400 and 600 nm. In one embodiment, two of the biomarker genes are amplified in the same reaction vessel.

In another aspect, the present invention provides a method of diagnosing a bacterial or viral infection in a patient with systemic inflammatory response syndrome [SIRS], comprising the steps of a) selecting a blood sample from a patient presenting clinical symptoms of systemic inflammatory response syndrome [SIRS], and quantitatively determining the presence of a diagnostic score indicative of a bacterial or viral infection based on the measured expression levels, e.g., absolute expression levels or relative expression levels as compared to control, e.g., housekeeping, genes, of at least two biomarker genes in the patient's blood selected from the group consisting of IFI27, GPAA1, HK3, TNIP1, and LAX1; (i) where the levels of the biomarker genes is measured by the amplification and detection of a subsequence of mRNA encoding the biomarker genes and wherein the score is quantitatively determined to be diagnostic by virtue of its exceeding a threshold indicative of a likelihood ratio of a bacterial or a viral infection of at least 2 in comparison with a reference population, wherein the threshold value is generated by the quantitative comparison of biomarker gene expression level scores of at least 100 patients known to have a diagnosis of SIRS as well as a bacterial or a viral infection, and 100 healthy controls; (ii) wherein the amplification and detection arises from the use of amplification primer pairs in the presence of undigested genomic DNA and fluorescent probes that bind to the amplified biomarker gene subsequence, and (iii) where the primer pairs and probes used to amplify the biomarker genes are selected from the group of primer and probe triplet member combinations consisting of AGTCACTGGGAGCAACTG (SEQ ID NO: 1), ACCAAGTTCATCCTGGGCTCCATT (SEQ ID NO: 2), and CAATGACAGCCGCAATGG (SEQ ID NO: 3) (triplet IFI27-B); AGTGACCAGTGTGGCCAAAGT (SEQ ID NO: 4), CCTCTGGCTCTGCCGTAGTTTTGCC (SEQ ID NO: 5), and TCCAATCACAACTGTAGCAATCCT (SEQ ID NO: 6) (triplet IFI127-3AA); AGTGACCAGTGTGGC-CAAAGT (SEQ ID NO: 7), AGGGGCAAAAC-TACGGCAGAGCCAG (SEQ ID NO: 8), and TCCAATCACAACTGTAGCAATCCT (SEQ ID NO: 9) (triplet IFI27-3C); AGTGACCAGTGTGGCCAAAGT (SEQ ID NO: 10), AGGGGCAAAACTACGGCAGAGCCA (SEQ ID NO: 11), and TCCAATCACAACTGTAGCAATCCT (SEQ ID NO: 12) (triplet IFI27-3D); CCCTCATTTCCTGGACCAAA (SEQ ID NO: 13), CTGCTGAGAGATGCCATTCGGAGG (SEQ ID NO: 14), and AACCACGTCGATGTTGTAGG (SEQ ID NO: 15) (triplet HK3-A); TGCTGAGAGATGCCATTCG (SEQ ID NO: 16), ATCGACGTGGTTGCTGTGGTGAA (SEQ ID NO: 17), and CTACAACTAGCCCAACCTCAC (SEQ ID NO: 18) (triplet HK3-B); TTTAGGTGCAGTGGTGTGG (SEQ ID NO: 19), CCTCCGAATGGCATCTCTCAGCAG (SEQ ID NO: 20), and GTGCCCACTGTGTCGTT (SEQ ID NO: 21) (triplet HK3-C-NEW); TCCAAGGTGCACAAGAATGA (SEQ ID NO: 22), ATTCTGCAGACCCTGTGTGAGCAG (SEQ ID NO: 23), and TCAGAGCCTCGTTCTCCTT (SEQ ID NO: 24) (triplet TNIP1-A); TCCAAGGTGCACAAGAATGA (SEQ ID NO: 25), TGTGAGCAGCTTCGGAAGGAGAAC (SEQ ID NO: 26), and ATCCAACTTGGCCTTCAGAG (SEQ ID NO: 27) (triplet TNIP-C); GGAGTATGCGCATTTTCAGTACTG (SEQ ID NO: 28), AGAGCCCGGAGCATGTGCCCTC (SEQ ID NO: 29), and GCATGGATGTGGGCTGTATG (SEQ ID NO: 30) (triplet LAX1-D); GGAGTATGCGCATTTTCAGTACTG (SEQ ID NO: 31), CCCGGAGCATGTGCCCTCCC (SEQ ID NO: 32), and GCATGGATGTGGGCTGTATG (SEQ ID NO: 33) (triplet LAX1-E); GGAGTATGCGCATTTTCAGTACTG (SEQ ID NO: 34), CCGGAGCATGTGCCCTCCCA (SEQ ID NO: 35), and GCATGGATGTGGGCTGTATG (SEQ ID NO: 36) (triplet LAX1-F); GGAGTATGCGCATTTTCAGTACTG (SEQ ID NO: 37), AGCATGTGCCCTCCCAAGCAGG (SEQ ID NO: 38), and GCATGGATGTGGGCTGTATG (SEQ ID NO: 39) (triplet LAX1-G); TCCTGGTCCTTGGTCTCAA (SEQ ID NO: 40), CTGCATCCACAGTTCCAGAGCCT (SEQ ID NO: 41), and TGATGGGGGAAGGGGTAC (SEQ ID NO: 42) (triplet GPAA1-WN-Y), including variants of the combination triplet members wherein the variants of the members comprise 95% or greater sequence identity to the members in the above tables and the primer and probe variants have a GC content of between 45 and 65%.

In one embodiment, one of the biomarker genes is GPAA1 or IF127. In one embodiment, the probes are labeled with a fluorophore having a maximum fluorescent emission of between 400 and 600 nm. In one embodiment, the score is further based on the expression level of the biomarker gene CTSB, wherein the CTSB biomarker gene is detected by a combination of three DNA sequences consisting of a forward primer, a reverse primer, and a fluorescent probe having the sequences ACTTCTACAACGTGGACATGAG (SEQ ID NO: 43), AGGCTATGTGGTACCTTCCTGGGT (SEQ ID NO: 44), and GGTCCTCGGTAAACATAACTCTC (SEQ ID NO: 45).

DETAILED DESCRIPTION OF THE INVENTION

Introduction

Figure 1:
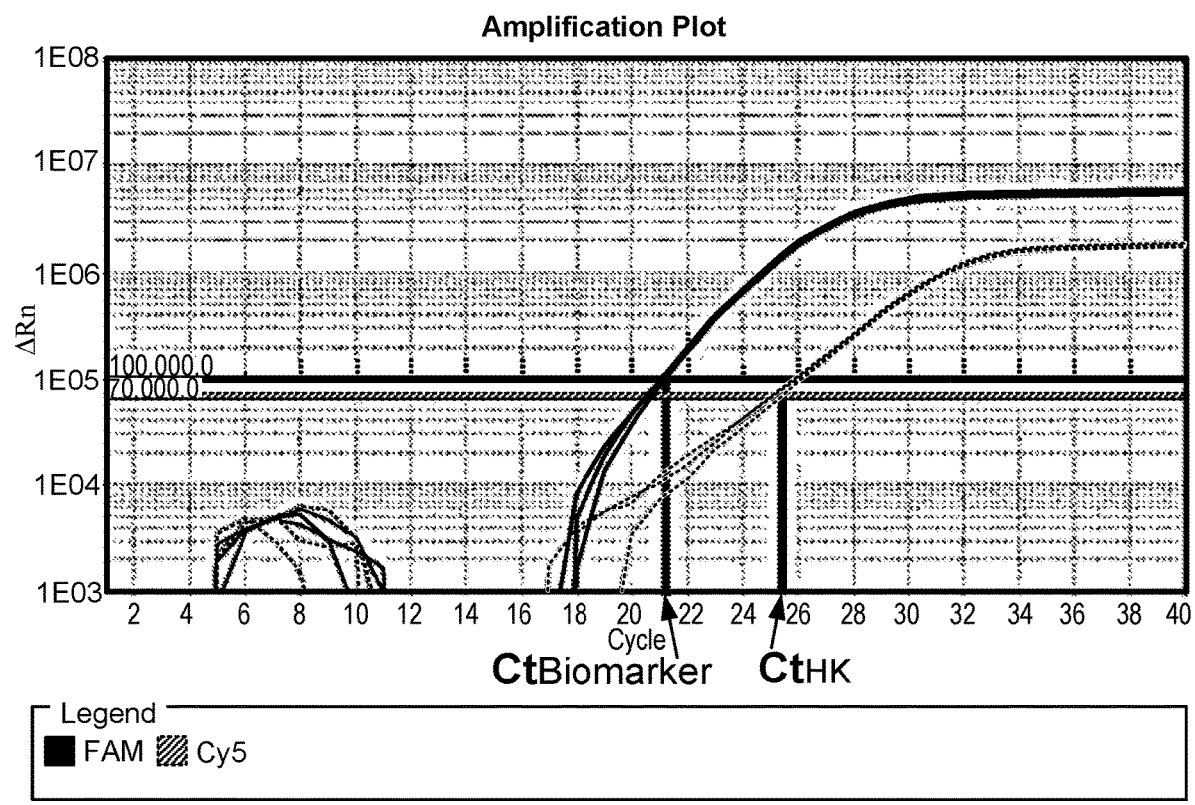
FIG. 1: Generation of Ct values for biomarker and housekeeping genes by software provided by real time PCR instrument. DeltaCt=(Ct Biomarker)–(Ct HK).

This invention provides for primer and probe triplet member combinations that are useful for the diagnosis and subsequent treatment of SIRS. The described combinations are derived from subsequences of mRNA encoding inflammation-sensitive biomarker genes of patient origin. The combinations are selected for their ability to efficiently amplify and detect their target sequences without the need to first degrade or otherwise remove host genomic DNA. Methods of using the triplet member combinations are also provided, e.g. for selecting and treating patients presenting symptoms of SIRS, as are genetic amplification systems that can be used for diagnosing and treating patients.

Approaches to diagnosing different forms of SIRS, i.e., among infection-negative SIRS and SIRS of bacterial or viral origin, can rely on methods of detecting mRNA levels of specific biomarker genes to evaluate host response. Such approaches can provide rapid and accurate indications of the etiology of the SIRS symptoms, outperforming other techniques such as the direct detection of pathogens.

Despite their efficacy, however, such approaches can be limited by the potential presence of genomic DNA in the assay medium. It is often necessary to remove genomic DNA in order to minimize the likelihood of hybridization of primers and probes to it, which can interfere with the performance of RT-PCR. Removal of genomic DNA from the sample can be performed, e.g., by treating it with nucleases such as DNAse I or by taking steps to purify the RNA away from any potentially contaminating DNA, e.g., by column centrifugation. Even when such steps are performed, it is often impossible to remove all of the gDNA from the sample. Together, these steps can be costly as well as time- and labor-intensive and are thus highly undesireable, particularly in situations where extremely short turnaround times are critical.

The present invention is based on the surprising discovery that certain triplet combinations (forward primer, reverse primer, and probe) exist that enable the performance of amplification assays, e.g., TaqMan-based assays, for the quantification of SIRS biomarker mRNA levels even in the presence of genomic DNA. The triplets thus allow the rapid detection of expression levels of biomarker genes even in the absence of steps to digest or remove genomic DNA. The biomarker expression levels can then be compared to the levels of baseline housekeeping genes and used to form biomarker scores that permit a determination of whether the SIRS is infection positive or negative, and, if positive, of viral or bacterial origin, allowing appropriate treatment regimens to be instituted rapidly.

Definitions

"SIRS," or "Systemic Inflammatory Response Syndrome," refers to a suite of clinical features resulting from a major inflammatory response to a non-specific acute insult such as infection, trauma, burns, ischemia, or surgery. SIRS is officially defined as the presence of at least two features including fever or hypothermia, elevated heart rate, elevated respiratory rate, or abnormal white blood cell count. However, it will be appreciated that, for the purposes of the present invention, SIRS can encompass patients displaying less than two of these criteria, but where a medical professional suspects nevertheless the presence of, or potential for, SIRS. As used herein, SIRS includes SIRS of any origin, including infectious SIRS, whether of bacterial or viral origin ("bacterial SIRS" or "viral SIRS"), or infection-negative SIRS.

As used herein, the terms "triplet", "triplet members", "triplet combination," or "triplet member combination" refers to sets of three polynucleotides that can be used together to amplify and quantify subsequences of SIRS biomarkers, e.g., quantify biomarker mRNA levels in qRT-PCR assays, in the presence of genomic DNA. In particular, the term refers to the sets of forward primers, reverse primers, and probes as shown in Table I and in SEQ ID NOs. 1-45, for the genes IFI27, HK3, TNP1, LAX1, GPAA1, and CTSB. The polynucleotides can have the exact sequences as shown in SEQ ID NOs. 1-45, but triplet combinations can also include variants and derivatives of SEQ ID NOs. 1-45, including substitutions, deletions, and insertions, e.g., sequences with 95%, 96%, 97%, 98%, 99%, or more sequence identity with SEQ ID NOs. 1-45, and in any combination within a given triplet, e.g., one, two, or all of the sequences within a given triplet can have the sequence shown as SEQ ID NOs. 1-45 or can be a variant showing 95%, 96%, 97%, 98%, 99%, or more sequence identity with any of SEQ ID NOs. 1-45. Sequences that are complementary to SEQ ID NOs. 1-45, or to derivatives or variants thereof, can be used as well. One of skill in the art can readily assess the suitability of any variant or derivative for use in the present invention. In particular, as long as the sequence can be used to efficiently and quantitatively amplify mRNA corresponding to a subsequence of one of the SIRS biomarker genes in the presence of genomic DNA as described herein, it can be used.

An "antimicrobial" refers to any compound or therapy that can be used to treat microbial infections, including "antibiotic" or "antibacterial" agents to treat bacterial infections, and "antiviral" agents to treat viral infections. For example, the present methods and compositions can be used to diagnose infection positive SIRS in patients, and, further, to diagnose viral or bacterial SIRS. Once such a diagnosis has been made, and in view of other clinical data, an antimicrobial agent, e.g., antibiotic or antiviral agent, can be administered to treat the bacterial or viral infection.

As used herein, the term "likelihood ratio" is the probability that a given test result would be observed in a subject with a condition of interest divided by the probability that that same result would be observed in a patient without the condition of interest. See below for more details.

The term "nucleic acid" or "polynucleotide" refers to primers, probes, oligonucleotides, template RNA or cDNA, genomic DNA, amplified subsequences of biomarker genes, or any polynucleotide composed of deoxyribonucleic acids (DNA), ribonucleic acids (RNA), or any other type of polynucleotide which is an N-glycoside of a purine or pyrimidine base, or modified purine or pyrimidine bases in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions can be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., Mol. Cell. Probes 8:91-98 (1994)). "Nucleic acid", "DNA" "polynucleotides, and similar terms also include nucleic acid analogs. The polynucleotides are not necessarily physically derived from any existing or natural sequence, but can be generated in any manner, including chemical synthesis, DNA replication, reverse transcription or a combination thereof.

"Primer" as used herein refers to an oligonucleotide, whether occurring naturally or produced synthetically, that is capable of acting as a point of initiation of synthesis when placed under conditions in which synthesis of a primer extension product which is complementary to a nucleic acid strand is induced i.e., in the presence of nucleotides and an agent for polymerization such as DNA polymerase and at a suitable temperature and buffer. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification such as a TaqMan real-time quantitative RT-PCR of the invention. The primers herein are selected to be substantially complementary to the different strands of each specific sequence to be amplified, and a given set of primers, e.g., within a triplet of the invention, will act together to amplify a subsequence of the corresponding biomarker gene that encompasses the probe that completes the triplet. Notably, the preferred primers of the invention can be used in quantitative RT-PCR assays, e.g., TaqMan assays, to efficiently amplify target sequences even in the presence of genomic DNA.

A "probe" as used herein refers to an oligonucleotide that is complementary to a subsequence of a biomarker gene such that it binds to the gene within the area delimited by a set of primers as disclosed herein. For use in the present methods, probes are typically composed of DNA, and for TaqMan or other probe-based quantitative real-time PCR assays they are derivatized with fluorescent or other moieties that allow the real-time monitoring of product accumulation. For example, in a TaqMan assay, a probe can contain a 5' fluorescent moiety and a 3' quenching moiety, such that when the probe initially binds to a template it emits minimal levels of fluorescence due to quenching by the 3' moiety, but the extension of a primer bound to the same template will lead to the separation of the 5' and 3' moieties of the probe due to the 5' nuclease of Taq polymerase, resulting in an increase in fluorescence intensity that can be detected when using appropriate instrumentation.

The term "gene" refers to the segment of DNA involved in producing a polypeptide chain. It can include regions preceding and following the coding region (leader and trailer) as well as intervening sequences (introns) between individual coding segments (exons).

As used herein, a "biomarker gene" or "biomarker" refers to a gene whose expression is correlated with the presence of absence of SIRS or of symptoms of SIRS, or with particular forms of SIRS, e.g., infection negative SIRS, viral SIRS, or bacterial SIRS, in patients. It will be appreciated that the biomarker gene expression need not be correlated with any of these features in all patients; rather, a correlation will exist at the population level, such that the level of expression, as measured, e.g., as a Ct or a delta Ct vis-a-vis the expression level of a housekeeping gene, is sufficiently correlated within the overall population of individuals with SIRS, infection negative SIRS, viral SIRS, or bacterial SIRS, etc. that it can be combined with the expression levels of other biomarker genes and used to calculate a biomarker gene score. Preferred biomarker genes for the purposes of the present invention include IFI27, GPAA1, HK3, TNIP1, LAX1, and CTSB.

A "biomarker gene score" or "biomarker score" refers to the value that is calculated from the measured expression levels of a plurality of biomarker genes, e.g., 2, 3, 4, 5, 6, 7, 8, 9 10 or more individual biomarker genes. The biomarker score can be calculated from, e.g., the Ct values or delta Ct values of the individual biomarker genes, for example by taking the geometric mean of the delta Ct values for all of the included biomarker genes, but it can be calculated in a number of other ways known to those of skill in the art. The "biomarker gene score" can be used to determine the likelihood, e.g., the likelihood ratio, of a given patient having infection negative SIRS, viral SIRS, or bacterial SIRS, etc., by virtue of the score surpassing or not a given threshold value for the SIRS value in question, as described in more detail elsewhere herein.

"Conservatively modified variants" refers to nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

One of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles. In some cases, conservatively modified variants can have an increased stability, assembly, or activity.

As used in herein, the terms "identical" or percent "identity," in the context of describing two or more polynucleotide sequences, refer to two or more sequences or specified subsequences that are the same. Two sequences that are "substantially identical" have at least 60% identity, preferably 65%, 70%, 75%, 80%, 85%, 90%, 91%, 92%, 93, 94%, 95%, 96%, 97%, 98%, 99%, or 100% identity, when compared and aligned for maximum correspondence over a comparison window, or designated region as measured using a sequence comparison algorithm or by manual alignment and visual inspection where a specific region is not designated. With regard to polynucleotide sequences, this definition also refers to the complement of a test sequence. The identity can exists over a region that is at least about 10, 15, 20, 25, 30, 35, 40, 45, 50, or more nucleotides in length. In some embodiments, percent identity is determined over the full-length of the nucleic acid sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST 2.0 algorithm and the default parameters discussed below are used.

A "comparison window", as used herein, includes reference to a segment of any one of a number of contiguous positions, e.g. a segment of 10, 11, 12, 13, 14, 15, 16, 17, 18, 19, 20, 21, 22, 23, 24, 25, 30, 35, 40, 45, or 50 nucleotides, in which a sequence can be compared to a reference sequence of the same number of contiguous positions after the two sequences are optimally aligned.

An algorithm for determining percent sequence identity and sequence similarity is the BLAST 2.0 algorithm, which is described in Altschul et al., (1990) J. Mol. Biol. 215: 403-410. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89:10915 (1989)).

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Patients

The present methods can be performed with any patient with a diagnosis of SIRS, who presents some or all characteristics of SIRS, or where there is any suspicion for any reason of the presence of or potential for SIRS by a medical professional. Criteria for SIRS include, inter alia: fever or hypothermia (>38° C. or <36° C.), tachycardia (>90 beats per minute), tachypnea (>20 breaths per minute or $PaCO_2$<32 mm Hg), and abnormal white blood cell count (>12,000/mm$^3$ or <4,000/mm$^3$ or >10% bands). Preferably, the patient shows at least two of these criteria, but it will be appreciated that the present methods and compositions can be used with patients meeting any of the criteria, or presenting with any typical symptoms of acute infection, such as malaise, fevers, chills, cough, abdominal pain, etc.

To select a patient for the present methods, when one or more, preferably two or more, criteria of SIRS are met, an assessment is made as to whether the patient has a biomarker score that exceeds a threshold indicating their SIRS status. It will be appreciated that the determination of the biomarker score, and the amplification-based assays underlying the score, can be performed in conjunction with the diagnosis of SIRS or of a suspicion of SIRS, e.g., ordered directly by the physician making the diagnosis, or can be assessed independently, e.g., by an independent laboratory.

Sample Preparation

To assess the biomarker status of the patient, a biological sample is obtained from the patient, e.g. a blood sample is taken by a phlebotomist, in a way that allows the RNA to be collected and preserved. For example, in a preferred embodiment, a blood sample is collected directly into a tube prefilled with a solution that can immediately stabilize RNA from blood cells within the sample. One suitable tube is the PAXgene Blood RNA Tube (QIAGEN, BD cat. No. 762165), although any tube capable of preserving RNA can be used, a number of which are known to those of skill in the art. Using the PAXgene Blood RNA Tube, RNA can be preserved, e.g., for three days at room temperature, for five days at 4° C., and for up to eight years when frozen. In addition to blood, e.g., whole blood, peripheral blood, or serum, other biological samples that can be used for the purposes of the invention, including, inter alia, plasma, saliva, urine, sweat, nasal swab, rectal swab, ascitic fluid, peritoneal fluid, synovial fluid, amniotic fluid, cerebrospinal fluid, and tissue biopsy. Typically, the biological sample comprises whole blood, or blood cells such as mature, immature or developing leukocytes, including lymphocytes, polymorphonuclear leukocytes, neutrophils, monocytes, reticulocytes, basophils, coelomocytes, hemocytes, eosinophils, megakaryocytes, macrophages, dendritic cells natural killer cells, or fraction of such cells (e.g., a nucleic acid or protein fraction).

Once blood has been collected and preserved, RNA can be extracted using any method, so long that it permits the preservation of the RNA for subsequent reverse transcription and quantitative PCR so as to determine the relative expression levels of the biomarker genes of the invention and of any control genes to be used, e.g., housekeeping genes used for the calculation of the delta Ct values for the biomarkers and subsequent determination of the biomarker score. Suitable housekeeping genes are well known in the art and may include, e.g., 18S (18S rRNA, e.g., HGNC (Human Genome Nomenclature Committee) nos. 44278-44281, 37657), ACTB (Actin beta, e.g., HGNC no. 132)), KPNA6 (Karyopherin subunit alpha 6, e.g., HGNC no. 6399), or RREB1 (ras-responsive element binding protein 1, e.g., HGNC no. 10449). In one embodiment, RNA is extracted from preserved blood cells manually. In another embodiment, RNA is extracted using a robotic apparatus, such as Qiacube (QIAGEN) with a commercial RNA extraction kit.

Using the present methods, in particular using the herein-described triplet primer-probe combinations, it is possible to perform the subsequent amplification steps in the presence of genomic DNA, meaning that steps such as the removal of genomic DNA using DNAse or through column centrifugation are not necessary and the RNA can thus be used directly in the assays.

Amplification

Once the RNA has been extracted, it is reverse transcribed to cDNA and amplified in a quantitative real-time PCR assay in order to determine the expression level of the SIRS biomarkers in question. Any probe-based quantitative PCR system or approach can be used or adapted for the purposes of the invention, e.g., internal DNA detection switch, MacMan probes, flip probes, and, preferably, TaqMan probes (see, e.g., Murray et al. (2014) J. Mol Diag. 16:6, pp 627-638).

TaqMan is a quantitative real-time amplification system that requires two primers (a forward and a reverse primer) and a probe (TaqMan probe) that is complementary to the PCR product of the forward and reverse primers and that also has a reporter fluorescent dye on its 5' end and a quencher on its 3' end. When the probe is intact, the fluorescence emitted by the 5' dye is quenched by the 3' quencher through FRET (fluorescence resonance energy transfer), thereby greatly reducing the fluorescent signal. In contrast, when the probe anneals downstream of one of the primer sites and is cleaved by the 5' nuclease activity of Taq polymerase during the extension phase of the PCR, the reporter dye is separated from the quencher and the fluorescence intensity in the reaction mixture increases. As such, the fluorescence intensity in the reaction is proportional to the progress of the PCR and, accordingly, to the quantity of starting biomarker RNA.

A number of TaqMan systems, assays, reagents, and kits have been developed, any one of which can be used in the present methods, e.g., according to the manufacturer's instructions. For example, MGB TaqMan probes, e.g., containing a FAM or VIC dye, a nonfluorescent 3' quencher, and a minor groove binder, can be used, as can other quenchers such as QSY quenchers, fluorescent quenchers such as TAMRA, or dark quenchers such as BHQ-1, BHQ-2, or Dabcyl. Other 5' dyes that can be used include, but are not limited to, ABY, JUN, CY5, Cy5.5, TET, HEX, Cy3, Texas Red, ROX, and TEX615, and other 3' quenchers include, but are not limited to, Iowa Black FQ and Iowa Black RQ. Such probes and systems are well known to those of skill in the art, and are supplied by various manufacturers such as Applied Biosystems (Thermo Fisher Scientific), Sigma-Aldrich, Integrated DNA Technologies, and others. In a preferred embodiment, the probe is labeled with a fluorophore that has a maximum fluorescent emission of between 400 and 600 nm.

The primers and probes of the invention can be obtained in any of a number of ways that are well known to those of skill in the art. For example, primers can be synthesized in the laboratory using an oligo synthesizer, e.g., as sold by Applied Biosystems, Biolytic Lab Performance, Sierra Biosystems, or others. Alternatively, primers and probes with any desired sequence and/or modification can be readily ordered from any of a large number of suppliers, e.g., ThermoFisher, Biolytic, IDT, Sigma-Aldritch, GeneScript, etc.

In a preferred embodiment, the RNA extracted from the cells is added to a Master Mix (e.g., RNA-to-Ct 1-Step Kit, or TaqMan Fast Virus 1-Step Master Mix from ThermoFisher Scientific, although 2-step kits can be used as well) that includes all the components needed for reverse transcription of the RNA and amplification, e.g., RNA transcriptase, DNA polymerase, $Mg^{2+}$, buffer, etc. For example, aliquots of the master mix, of the TaqMan reagents, and the RNA templates are dispensed to the wells of PCR plates, and PCR reactions can be carried out using any real-time PCR thermal cycler, e.g., QuantStudio 6 Flex Real-time PCR system (QS6).

With each cycle of the reaction, with each new amplicon generated, the 5' reporter and the 3' quencher are separated due to the 5' nuclease activity of Taq polymerase, thereby leading to an increase in fluorescence as the reaction mixture is exposed to light at the appropriate wavelength, and the increase in fluorescence is detected by the instrument. The fluorescent signal is detected at the end of each cycle, for up to 40 cycles. The software for the real-time PCR cycler then analyzes the collected fluorescent signal intensities and generates Ct (Cycle Threshold) values for each sample and each biomarker tested. The higher the RNA levels are, the lower are the Ct values.

The amplification reactions as described herein are performed with particular primer and probe combinations that enable efficient amplification of subsequences of the biomarkers even in the presence of genomic DNA. By "efficient," it is meant, for example, that the amplification of the target subsequences reaches a minimum of $1.4 \times 10^{11}$ copies after 40 cycles in the presence of at least 0.8×10' mM undigested genomic DNA. The sets of forward primer+ reverse primer+probe that work together to amplify the biomarker subsequences even in the presence of genomic DNA are referred to herein as "triplets", or "triplet member combinations" or "triplet combinations." It will be appreciated that the vast majority of potential primers and probes for amplifying subsequences within the biomarkers disclosed herein, i.e., IFI27, HK3, LAX1, GPAA1, TNIP1, CTSB, or for other potential SIRS biomarkers, do not permit efficient amplification in the presence of genomic DNA, and that the specific triplets disclosed herein have been specifically identified based on this rare ability. The primers and probes disclosed herein for use in the invention have been validated to give no or only insignificant background on NTC (no template control), and to give no, or only insignificant levels of, background on gDNA, even in the presence of substantial amounts of gDNA, e.g., when the carryover of gDNA is 100% of the amount of RNA.

The preferred primers and probes for use in the invention are as shown in Table I:

TABLE I

| Gene | P:P Combination | Function | Sequence | Sequence ID No. |
|---|---|---|---|---|
| | IFI27-B | Forward | AGTCACTGGGAGCAACTG | 1 |
| | | Probe | ACCAAGTTCATCCTGGGCTCCATT | 2 |
| | | Reverse | CAATGACAGCCGCAATGG | 3 |
| | IFI27-3AA | Forward | AGTGACCAGTGTGGCCAAAGT | 4 |
| | | Probe | CCTCTGGCTCTGCCGTAGTTTTGCC | 5 |
| | | Reverse | TCCAATCACAACTGTAGCAATCCT | 6 |
| IFI27 | | | | |
| | IFI27-3C | Forward | AGTGACCAGTGTGGCCAAAGT | 7 |
| | | Probe | AGGGGCAAAACTACGGCAGAGCCAG | 8 |
| | | Reverse | TCCAATCACAACTGTAGCAATCCT | 9 |

TABLE I-continued

| Gene | P:P Combination | Function | Sequence | Sequence ID No. |
|---|---|---|---|---|
| | IFI27-3D | Forward | AGTGACCAGTGTGGCCAAAGT | 10 |
| | | Probe | AGGGGCAAAACTACGGCAGAGCCA | 11 |
| | | Reverse | TCCAATCACAACTGTAGCAATCCT | 12 |
| | HK3-A | Forward | CCCTCATTTCCTGGACCAAA | 13 |
| | | Probe | CTGCTGAGAGATGCCATTCGGAGG | 14 |
| | | Reverse | AACCACGTCGATGTTGTAGG | 15 |
| HK3 | HK3-B | Forward | TGCTGAGAGATGCCATTCG | 16 |
| | | Probe | ATCGACGTGGTTGCTGTGGTGAA | 17 |
| | | Reverse | CTACAACTAGCCCAACCTCAC | 18 |
| | HK3-C-NEW | Forward | TTTAGGTGCAGTGGTGTGG | 19 |
| | | Probe | CCTCCGAATGGCATCTCTCAGCAG | 20 |
| | | Reverse | GTGCCCACTGTGTCGTT | 21 |
| | TNIP1-A | Forward | TCCAAGGTGCACAAGAATGA | 22 |
| | | Probe | ATTCTGCAGACCCTGTGTGAGCAG | 23 |
| TNIP1 | | Reverse | TCAGAGCCTCGTTCTCCTT | 24 |
| | TNIP-C | Forward | TCCAAGGTGCACAAGAATGA | 25 |
| | | Probe | TGTGAGCAGCTTCGGAAGGAGAAC | 26 |
| | | Reverse | ATCCAACTTGGCCTTCAGAG | 27 |
| | LAX1-D | Forward | GGAGTATGCGCATTTTCAGTACTG | 28 |
| | | Probe | AGAGCCCGGAGCATGTGCCCTC | 29 |
| | | Reverse | GCATGGATGTGGGCTGTATG | 30 |
| | LAX1-E | Forward | GGAGTATGCGCATTTTCAGTACTG | 31 |
| | | Probe | CCCGGAGCATGTGCCCTCCC | 32 |
| | | Reverse | GCATGGATGTGGGCTGTATG | 33 |
| LAX | | | | |
| | LAX1-F | Forward | GGAGTATGCGCATTTTCAGTACTG | 34 |
| | | Probe | CCGGAGCATGTGCCCTCCCA | 35 |
| | | Reverse | GCATGGATGTGGGCTGTATG | 36 |
| | LAX1-G | Forward | GGAGTATGCGCATTTTCAGTACTG | 37 |
| | | Probe | AGCATGTGCCCTCCCAAGCAGG | 38 |
| | | Reverse | GCATGGATGTGGGCTGTATG | 39 |
| GPAA1 | GPAA1-WN-Y | Forward | TCCTGGTCCTTGGTCTCAA | 40 |
| | | Probe | CTGCATCCACAGTTCCAGAGCCT | 41 |
| | | Reverse | TGATGGGGAAGGGGTAC | 42 |
| CTSB | CTSB-B | Forward | ACTTCTACAACGTGGACATGAG | 43 |
| | | Probe | AGGCTATGTGGTACCTTCCTGGGT | 44 |
| | | Reverse | GGTCCTCGGTAAACATAACTCTC | 45 |

It will be appreciated, however, that derivatives and variants of any of these sequences can also be used, including sequences with 95%, 96%, 97%, 98%, 99%, or higher sequence identity to any of SEQ ID NOs 1-45, including substitutions, e.g., conservative substitutions, deletions, and insertions, and including natural or modified nucleotides, as well as sequences that are complementary to SEQ ID NOs 1-45, and substitutions, deletions, insertions, and other derivatives and variants of sequences complementary to SEQ ID NOs 1-45.

Generally, any polynucleotides corresponding to SEQ ID NOs. 1-45 and derivatives, variants thereof can be used, including sequences complementary to SEQ ID NOs. 1-45, provided that they can allow efficient amplification of SIRS biomarker mRNA subsequences in the presence of genomic DNA, as described herein. In preferred embodiments, the primers and probe will have a GC content of between 45% and 65%.

The biomarkers used in the present methods correspond to genes whose expression levels correlate with the presence or absence of an infection in patients presenting SIRS symptoms, and, among those with infection-positive SIRS, with a viral or bacterial origin of infection. It will be appreciated that the expression level of the individual biomarkers can be elevated or depressed relative to in healthy individuals without SIRS or SIRS symptoms; what is important is that the expression level of the biomarker is positively or inversely correlated with the presence or absence of SIRS in the overall population of individuals with the condition, or with the presence or absence of an infection when SIRS is present, or, with a viral or bacterial cause of infection-positive SIRS, and that the expression levels as measured using the herein described methods, and as expressed as, e.g., a Ct value or a Delta Ct value, can be combined with the levels of other biomarker genes to generate a biomarker score that can be used for the diagnostic or therapeutic purposes described herein.

The biomarkers of the invention, whose subsequences can be amplified in accordance with the present disclosure, include the following genes, together with their reference numbers in the database of the Human Genome Nomenclature Committee and the Entrez Gene numbers of the human genes, are shown in Table II.

TABLE II

| Biomarker | Full gene name | Human Genome Nomenclature Reference No. | Entrez Gene number |
|---|---|---|---|
| IFI27 | Interferon Alpha Inducible Protein 27 | 5397 | 3429 |
| GPAA1 | Glycosylphosphatidylinositol Anchor Attachment 1 | 4446 | 8733 |
| HK3 | Hexokinase 3 | 4925 | 3101 |
| TNIP1 | TNFAIP3 Interacting Protein 1 | 16903 | 10318 |
| LAX1 | Lymphocyte Transmembrane Adaptor 1 | 26005 | 54900 |
| CTSB | Cathepsin B | 2527 | 1508 |

The levels of at least two of the biomarker genes as assessed using the herein-described triplet combinations are then combined to generate a biomarker score that will be used to assess the SIRS status of the patient, i.e., whether the SIRS is due to infection and, if so, whether the infection is of viral or bacterial origin, and thus to guide treatment decisions for the patient. At least 2 of the biomarkers shown in Table II will be used to generate the biomarker score, but in numerous embodiments more than 2 will be used, e.g., 3, 4, 5, or 6 of the biomarkers from Table II. It will be understood that any combination of 2, 3, 4, 5, or 6 of the herein-described biomarkers can be used, and that the measured levels of any 2 or more of them can be combined with the measured expression levels of other biomarkers. For example, the measured levels of 2 of the biomarkers shown in Table II can be combined with the measured levels of 2, 3, 4, 5, 6, 7, 8, or more other biomarkers (i.e. biomarkers not shown in Table II) to generate a biomarker score. In a preferred embodiment, the measured biomarkers will include GPAA1 and/or IFI27. Other biomarkers used to generate the biomarker score can include, inter alia, CEACAM1 (Carcinoembryonic antigen related cell adhesion molecule 1, e.g., HGNC no. 1814), ZDHHC19 (zinc finger DHHC-type containing 19, e.g., HGNC no. 20713), NMRK1 (nicitinamide riboside kinase 1, e.g., HGNC no. 26057), GNA15 (G protein subunit alpha 15, e.g., HGNC no. 4383), BATF (basic leucine zipper ATF-like transcription factor, e.g., HGNC no. 958), C3AR1 (complement C3a receptor 1, e.g., HGNC no. 1319), FAM214A (family with sequence similarity 214 member A, e.g., HGNC 25609), TGFBI (transforming growth factor beta induced, e.g., HGNC no. 11771), MTCH1 (mitochondrial carrier 1, e.g., HGNC no. 17586), RPGRIP1 (RPGR interacting protein 1, e.g., HGNC no. 13436), HLA-DPB1 (major histocompatibility complex, class II, DP beta 1, e.g., HGNC no. 4940), and JUP (junction plakoglobin, e.g., HGNC no. 6207).

It will be appreciated that, just as any combination of the biomarkers can be used in the present methods, where more than one triplet combination is disclosed for a given biomarker in Table I (e.g., for IFI27, the triplet combinations IFI27-B, IFI27-3AA, IFI27-3C, and IFI27-3D are disclosed), any of the provided triplets can be used for the amplification of the biomarker subsequences, without limitation.

Scoring

The biomarker genes selected for use and measured as described herein will be combined to generate a biomarker score. A score would be calculated by either taking the sum, product, or quotient of the gene levels, taken in terms of their absolute levels or their relative levels as compared to control genes, e.g., housekeeping genes, or by inputting them into a linear or nonlinear algorithm that incorporates at least the measured gene levels, e.g., the measured levels of 2, 3, 4, 5, 6, 7, 8, 9, 10 or more biomarker genes, into an interpretable score.

It will be appreciated that it is not necessary that all of the biomarkers will be elevated or depressed relative to control levels in a given patient to give rise to a determination of infection negative SIRS, or of SIRS of bacterial or viral origin; for example, for a given biomarker level there can be some overlap between individuals falling into different SIRS categories. However, collectively the combined levels for all of the biomarker genes included in the assay will give rise to a biomarker score that, if it surpasses a threshold, e.g., a threshold derived from at least 50, 100, 150, 200, 250, 300, 350, 400, 500 or more patients with SIRS of bacterial, viral, or non-infectious origin, and/or of 50, 100, 150, 200, 250, 300, 350, 400, 500 or more control individuals without the target SIRS status, that allows a determination concerning the SIRS status of the patient, or of a likelihood or probability concerning the SIRS status of the patient. For example, for a diagnosis of bacterial SIRS, the threshold could be such that at across a population of at least 100 healthy controls and 100 patients with SIRS due to bacterial infection, at least 90% of the patients with bacterial infection are above the threshold. In certain embodiments, the biomarker score is calculated, based on the measured levels of the biomarkers in bacterial, viral, and/or non-infectious SIRS and in healthy controls, such that a score for a patient that surpasses the threshold indicates that the patient has a likelihood ratio of 1.5, 2, 2.5, 3, 3.5, 4, or more for the presence of a bacterial or viral infection, or for an absence of both a bacterial and viral infection (i.e. infection negative SIRS), compared to a reference population, or that there is a likelihood or probability of at least 70%, 80%, 85%, 90%, 95%, 96%, 97%, 98%, 99%, or higher of the patient having, e.g., an infection, or having specifically a bacterial or viral infection. It will be appreciated that in any given assay there can be more than one threshold, e.g., a threshold in one direction that indicates bacterial SIRS, and a threshold in the other direction that indicates viral SIRS.

As used herein, the term "likelihood" is used as a measure of whether subjects with a particular biomarker score actually have a condition (or not) based on a given mathematical model. An increased likelihood for example can be relative or absolute and can be expressed qualitatively or quantitatively. For instance, an increased risk can be expressed as simply determining the subject's biomarker score and placing the test subject in an "increased risk" category, based upon previous population studies. Alternatively, a numerical expression of the test subject's increased risk can be determined based upon a biomarker score analysis.

As used herein, the term "probability" refers strictly to the probability of class membership for a sample as determined by a given mathematical model and is construed to be equivalent to likelihood in this context.

In some embodiments, likelihood is assessed by comparing the level or abundance of individual biomarkers to one or more preselected or threshold levels, or of an overall biomarker score to one or more such levels. Threshold values can be selected that provide an acceptable ability to predict diagnosis, prognostic risk, treatment success, etc. In illustrative examples, receiver operating characteristic (ROC) curves are calculated by plotting the value of a variable versus its relative frequency in two populations in which a first population has a first condition or risk and a second population has a second condition or risk (called arbitrarily, for example, "healthy condition" and "SIRS," "healthy condition" and "infection negative SIRS," "healthy condition" and "infectious SIRS," "infection negative SIRS" and "infectious SIRS," "bacterial SIRS" and "viral SIRS", etc.).

For any particular biomarker, a distribution of biomarker levels for subjects with and without a disease will likely overlap, and some overlap will be present for biomarker scores as well. Under such conditions, a test does not absolutely distinguish a first condition and a second condition with 100% accuracy, and the area of overlap indicates where the test cannot distinguish the first condition and the second condition. A threshold value is selected, above which (or below which, depending on how a biomarker or biomarker score changes with a specified condition or prognosis) the test is considered to be "positive" and below which the test is considered to be "negative." The area under the ROC curve (AUC) provides the C-statistic, which is a measure of the probability that the perceived measurement will allow correct identification of a condition (see, e.g., Hanley et al., Radiology 143: 29-36 (1982).

Alternatively, or in addition, threshold values can be established by obtaining an earlier biomarker expression level, or a biomarker score, from the same patient, to which later results can be compared. In these embodiments, the individual in effect acts as their own "control group." In biomarker gene levels or biomarker scores that increase with condition severity or prognostic risk, an increase over time in the same patient can indicate a worsening of the condition or a failure of a treatment regimen, while a decrease over time can indicate remission of the condition or success of a treatment regimen.

In some embodiments, a positive likelihood ratio, negative likelihood ratio, odds ratio, and/or AUC or receiver operating characteristic (ROC) values are used as a measure of a method's ability to predict risk or to diagnose a disease or condition. As used herein, the term "likelihood ratio" is the probability that a given test result would be observed in a subject with a condition of interest divided by the probability that that same result would be observed in a patient without the condition of interest. Thus, a positive likelihood ratio is the probability of a positive result observed in subjects with the specified condition divided by the probability of a positive results in subjects without the specified condition. A negative likelihood ratio is the probability of a negative result in subjects without the specified condition divided by the probability of a negative result in subjects with specified condition. The term "odds ratio," as used herein, refers to the ratio of the odds of an event occurring in one group (e.g., a healthy condition group) to the odds of it occurring in another group (e.g., an infection negative SIRS group, or a group with bacterial SIRS or viral SIRS), or to a data-based estimate of that ratio. The term "area under the curve" or "AUC" refers to the area under the curve of a receiver operating characteristic (ROC) curve, both of which are well known in the art. AUC measures are useful for comparing the accuracy of a classifier across the complete data range. Classifiers with a greater AUC have a greater capacity to classify unknowns correctly between two groups of interest (e.g., a healthy condition biomarker gene level or score and an infection-negative SIRS, infectious SIRS, or viral or bacterial SIRS biomarker gene level or score). ROC curves are useful for plotting the performance of a particular feature (e.g., any of the biomarker expression levels or biomarker scores described herein and/or any item of additional biomedical information) in distinguishing or discriminating between two populations (e.g., cases having a condition and controls without the condition). Typically, the feature data across the entire population (e.g., the cases and controls) are sorted in ascending order based on the value of a single feature. Then, for each value for that feature, the true positive and false positive rates for the data are calculated. The sensitivity is determined by counting the number of cases above the value for that feature and then dividing by the total number of cases. The specificity is determined by counting the number of controls below the value for that feature and then dividing by the total number of controls.

Although this refers to scenarios in which a feature is elevated in cases compared to controls, it also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to produce a single value, and this single value can be plotted in a ROC curve. Additionally, any combination of multiple features, in which the combination derives a single output value, can be plotted in a ROC curve. These combinations of features can comprise a test. The ROC curve is the plot of the sensitivity of a test against the specificity of the test, where sensitivity is traditionally presented on the vertical axis and specificity is traditionally presented on the horizontal axis. Thus, "AUC ROC values" are equal to the probability that a classifier will rank a randomly chosen positive instance higher than a randomly chosen negative one.

In some embodiments, at least two (e.g., 2, 3, 4, 5, 6, 7, 8, 9, 10, or more) biomarker genes are selected to discriminate between subjects with a first condition and subjects with a second condition with at least about 70%, 75%, 80%, 85%, 90%, 95% accuracy or having a C-statistic of at least about 0.70, 0.75, 0.80, 0.85, 0.90, 0.95.

In the case of a positive likelihood ratio, a value of 1 indicates that a positive result is equally likely among subjects in both the "condition" and "control" groups; a value greater than 1 indicates that a positive result is more likely in the condition group; and a value less than 1 indicates that a positive result is more likely in the control group. In this context, "condition" is meant to refer to a group having one characteristic (e.g., the presence of a healthy condition, SIRS, infection negative SIRS, bacterial SIRS, viral SIRS) and "control" group lacking the same characteristic. In the case of a negative likelihood ratio, a value of 1 indicates that a negative result is equally likely among subjects in both the "condition" and "control" groups; a value greater than 1 indicates that a negative result is more likely in the "condition" group; and a value less than 1 indicates that a negative result is more likely in the "control" group. In the case of an odds ratio, a value of 1 indicates that a positive result is equally likely among subjects in both the condition" and "control" groups; a value greater than 1 indicates that a positive result is more likely in the "condition" group; and a value less than 1 indicates that a positive result is more likely in the "control" group. In the case of an AUC ROC value, this is computed by numerical integration of the ROC curve. The range of this value can be 0.5 to 1.0. A value of 0.5 indicates that a classifier (e.g., a biomarker level or score) cannot discriminate between cases and controls, while 1.0 indicates perfect diagnostic accuracy. In certain embodiments, biomarker gene levels and/or biomarker scores are selected to exhibit a positive or negative likelihood ratio of at least about 1.5 or more or about 0.67 or less, at least about 2 or more or about 0.5 or less, at least about 5 or more or about 0.2 or less, at least about 10 or more or about 0.1 or less, or at least about 20 or more or about 0.05 or less.

In certain embodiments, the biomarker gene levels and/or biomarker scores are selected to exhibit an odds ratio of at least about 2 or more or about 0.5 or less, at least about 3 or more or about 0.33 or less, at least about 4 or more or about 0.25 or less, at least about 5 or more or about 0.2 or less, or at least about 10 or more or about 0.1 or less. In certain embodiments, biomarker gene levels and/or biomarker scores are selected to exhibit an AUC ROC value of greater than 0.5, preferably at least 0.6, more preferably 0.7, still more preferably at least 0.8, even more preferably at least 0.9, and most preferably at least 0.95.

In some cases, multiple thresholds can be determined in so-called "tertile," "quartile," or "quintile" analyses. In these methods, the "diseased" and "control groups" (or "high risk" and "low risk") groups are considered together as a single population, and are divided into 3, 4, or 5 (or more) "bins" having equal numbers of individuals. The boundary between two of these "bins" can be considered "thresholds." A risk (of a particular diagnosis or prognosis for example) can be assigned based on which "bin" a test subject falls into.

The phrases "assessing the likelihood" and "determining the likelihood," as used herein, refer to methods by which the skilled artisan can predict the presence or absence of a condition (e.g., a condition selected from healthy condition, infection-negative SIRS, viral SIRS, bacterial SIRS) in a patient. The skilled artisan will understand that this phrase includes within its scope an increased probability that a condition is present or absent in a patient; that is, that a condition is more likely to be present or absent in a subject. For example, the probability that an individual identified as having a specified condition actually has the condition can be expressed as a "positive predictive value" or "PPV." Positive predictive value can be calculated as the number of true positives divided by the sum of the true positives and false positives. PPV is determined by the characteristics of the predictive methods of the present invention as well as the prevalence of the condition in the population analyzed. The statistical algorithms can be selected such that the positive predictive value in a population having a condition prevalence is in the range of 70% to 99% and can be, for example, at least 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In other examples, the probability that an individual identified as not having a specified condition actually does not have that condition can be expressed as a "negative predictive value" or "NPV." Negative predictive value can be calculated as the number of true negatives divided by the sum of the true negatives and false negatives. Negative predictive value is determined by the characteristics of the diagnostic or prognostic method, system, or code as well as the prevalence of the disease in the population analyzed. The statistical methods and models can be selected such that the negative predictive value in a population having a condition prevalence is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some embodiments, a subject is determined to have a significant likelihood of having or not having a specified condition. By "significant likelihood" is meant that the subject has a reasonable probability (0.6, 0.7, 0.8, 0.9 or more) of having, or not having, a specified condition.

In some embodiments, data sets corresponding to the biomarker gene expression levels and biomarker scores of the invention are used to create a diagnostic or predictive rule or model based on the application of a statistical and machine learning algorithm, which produces the diagnostic score. Such an algorithm uses relationships between a biomarker profile and a condition selected from healthy condition, infection-negative SIRS, viral SIRS or bacterial SIRS observed in control subjects or typically cohorts of control subjects (sometimes referred to as training data), which provides combined control or reference biomarker profiles for comparison with the biomarker profiles of a subject. The data are used to infer relationships that are then used to predict the status of a subject, including the presence or absence of one of the conditions referred to above.

The term "correlating" generally refers to determining a relationship between one type of data with another or with a state. In various embodiments, correlating a given biomarker level or score with the presence or absence of a condition (e.g., a condition selected from a healthy condition, infection-negative SIRS, viral SIRS or bacterial SIRS) comprises determining the presence, absence or amount of at least one biomarker in a subject that suffers from that condition; or in persons known to be free of that condition. In specific embodiments, a set of biomarker levels, absences or presences is correlated to a global probability or a particular outcome, using receiver operating characteristic (ROC) curves.

In semi-quantitative methods, a threshold or cut-off value is suitably determined, and is optionally a predetermined value. In particular embodiments, the threshold value is predetermined in the sense that it is fixed, for example, based on previous experience with the assay and/or a population of affected and/or unaffected subjects, e.g., with a population of 50, 100, 150, 200, 250, 300, 350, 400, 450, 500, or more affected and/or unaffected subjects, i.e., subjects with infection-negative SIRS, viral SIRS or bacterial SIRS. Alternatively, the predetermined value can also indicate that the method of arriving at the threshold is predetermined or fixed even if the particular value varies among assays or can even be determined for every assay run.

For the statistical analyses described herein, e.g., for the selection of biomarkers to be included in the calculation of a score or in the calculation of a probability or likelihood of a particular SIRS status in a patient, as well as for diagnostic or therapeutic assessments made in view of a given biomarker score, other relevant information will also be considered, such as clinical data regarding one or more conditions suffered by each individual. This can include demographic information such as age, race, and sex; information regarding a presence, absence, degree, stage, severity or progression of a condition, phenotypic information, such as details of phenotypic traits, genetic or genetically regulated information, amino acid or nucleotide related genomics information, results of other tests including imaging, biochemical and hematological assays, other physiological scores such as a SOFA (Sequential Organ Failure Assessment) score, or the like.

In typical embodiments of the present methods, the scores are calculated based on the Ct (Cycle Threshold) values for each of the tested biomarkers. Ct values and their calculation are well known in the art, and they can be calculated, e.g., by the software of the real-time PCR thermal cycler. Typically, in addition to the Ct values for the selected biomarkers, Ct values are also generated for one or more housekeeping (HK) gene, i.e. a uniformly expressed gene that shows low variance under all conditions. The HK gene is used to normalize the RNA input in each PCR reaction. A Ct value is also generated for the HK gene or genes, and for each tested biomarker a normalized value, referred to as Delta Ct (corresponding to $Ct_{Biomarker}-Ct_{HK}$), is calculated. In preferred embodiments, the Delta Ct values for the different biomarker genes are used to calculate the biomarker score, e.g., using a custom validated algorithm. For example, the biomarker score can be generated using the geometric mean of the Delta Ct values for the different biomarkers.

Treatment

In view of a given biomarker score in a patient, e.g., when a biomarker score is calculated that suggests a relative likelihood of a particular form of SIRS such as viral or bacterial SIRS, methods are also provided for the management of the condition, e.g., viral SIRS or bacterial SIRS, for the prevention of further progression of the condition, e.g., bacterial SIRS or viral SIRS, or for the assessment of the efficacy of therapies in subjects for the condition, e.g., viral or bacterial SIRS. The management of SIRS conditions is generally highly intensive and can include identification and amelioration of the underlying cause and aggressive use of therapeutic compounds such as, antimicrobial agents, antibiotics, antiviral compounds, steroids, immune-modulating small molecules or proteins, or others. In addition, palliative therapies as described for example in Cohen and Glauser (1991, Lancet 338: 736-739) aimed at restoring and protecting organ function can be used such as intravenous fluids and oxygen and tight glycemic control. Therapies for SIRS are reviewed in Healy (2002, Ann. Pharmacother. 36(4): 648-54) and Brindley (2005, CJEM. 7(4): 227) and Jenkins (2006, J Hosp Med. 1(5): 285-295).

Typically, the therapeutic agents will be administered in pharmaceutical (or veterinary) compositions together with a pharmaceutically acceptable carrier and in an effective amount to achieve their intended purpose. The dose of active compounds administered to a subject should be sufficient to achieve a beneficial response in the subject over time such as a reduction in, or relief from, the symptoms of SIRS. The quantity of the pharmaceutically active compounds(s) to be administered can depend on the subject to be treated inclusive of the age, sex, weight and general health condition thereof. In this regard, precise amounts of the active compound(s) for administration will depend on the judgment of the practitioner. In determining the effective amount of the active compound(s) to be administered in the treatment or prevention of viral SIRS or bacterial SIRS, the medical practitioner or veterinarian can evaluate severity of any symptom associated with the presence of SIRS, including, e.g., inflammation, blood pressure anomaly, tachycardia, tachypnea fever, chills, vomiting, diarrhea, skin rash, headaches, confusion, muscle aches, seizures. In any event, those of skill in the art can readily determine suitable dosages of the therapeutic agents and suitable treatment regimens without undue experimentation.

The therapeutic agents can be administered in concert with adjunctive (palliative) therapies to increase oxygen supply to major organs, increase blood flow to major organs and/or to reduce the inflammatory response. Illustrative examples of such adjunctive therapies include non-steroidal anti-inflammatory drugs (NSAIDs), intravenous saline and oxygen.

Thus, the present invention contemplates the use of the methods and compositions described above and elsewhere herein in methods for treating, preventing or inhibiting the development of viral SIRS or bacterial SIRS in a subject. These methods generally comprise (1) correlating a reference biomarker score with the presence or absence of a condition selected from a healthy condition, infection-negative SIRS, viral SIRS, or bacterial SIRS, wherein the reference biomarker score evaluates at least two (e.g., 2, 3, 4, 5, 6, etc.) of the herein-described biomarker genes; (2) calculating a biomarker score of a sample from a patient; (3) determining a likelihood of the subject having or not having the condition based on the sample biomarker score and the reference biomarker score, and administering to the subject, on the basis that the subject has an increased likelihood of having infectious SIRS, e.g. bacterial SIRS or viral SIRS, an effective amount of an agent that treats or ameliorates the symptoms or reverses or inhibits the development of the bacterial or viral SIRS.

In some embodiments the methods and compositions of the present invention are used for monitoring, treatment and managing conditions that can lead to SIRS, illustrative examples of which include retained placenta, meningitis, endometriosis, shock, toxic shock (i.e., sequelae to tampon use), gastroenteritis, appendicitis, ulcerative colitis, Crohn's disease, inflammatory bowel disease, acid gut syndrome, liver failure and cirrhosis, failure of colostrum transfer in neonates, ischemia (in any organ), bacteremia, infections within body cavities such as the peritoneal, pericardial, thecal, and pleural cavities, burns, severe wounds, excessive exercise or stress, hemodialysis, conditions involving intolerable pain (e.g., pancreatitis, kidney stones), surgical operations, and non-healing lesions. In these embodiments, the methods of the present invention are typically used at a frequency that is effective to monitor the early development of SIRS, e.g., viral or bacterial SIRS, to thereby enable early therapeutic intervention and treatment of that condition.

The present invention can be practiced in the field of predictive medicine for the purposes of diagnosis or monitoring the presence or development of a condition selected from SIRS, infection-negative SIRS, viral SIRS, and bacterial SIRS in a subject, and/or monitoring response to therapy efficacy.

As used herein, the term "treatment regimen" refers to prophylactic and/or therapeutic (i.e., after onset of a specified condition) treatments, unless the context specifically indicates otherwise. The term "treatment regimen" encompasses natural substances and pharmaceutical agents (i.e., "drugs") as well as any other treatment regimen including but not limited to dietary treatments, physical therapy or exercise regimens, surgical interventions, and combinations thereof. In preferred embodiments, the treatment regimens of the invention will include the administration of antibacterial or antiviral compounds for the treatment of bacterial SIRS or viral SIRS, respectively.

The invention can also be practiced to evaluate whether a subject is responding (i.e., a positive response) or not responding (i.e., a negative response) to a treatment regimen. This aspect of the invention provides methods of correlating a biomarker score with a positive and/or negative response to a treatment regimen. These methods generally comprise: (a) calculating a biomarker score from a subject with a condition selected from infection-negative SIRS, viral SIRS, or bacterial SIRS following commencement of the treatment regimen, wherein the biomarker score is based on the expression levels of at least two (e.g., 2, 3, 4, 5, 6, etc.) of the herein-disclosed biomarker genes; and (b) correlating the biomarker score from the subject with a positive and/or negative response to the treatment regimen.

In some embodiments, the methods further comprise determining a first biomarker score from the patient prior to commencing the treatment regimen (i.e., a baseline profile), wherein the first biomarker score evaluates at least two (e.g., 2, 3, 4, 5, 6, etc.) of the herein-described biomarkers; and comparing the first sample biomarker score with a second sample biomarker score from the subject after commencement of the treatment regimen, wherein the second sample biomarker score evaluates for an individual biomarker in the first sample biomarker score a corresponding biomarker.

This aspect of the invention can be practiced to identify responders or non-responders relatively early in the treatment process, i.e., before clinical manifestations of efficacy. In this way, the treatment regimen can optionally be discontinued, a different treatment protocol can be implemented, and/or supplemental therapy can be administered. Thus, in some embodiments, a sample biomarker score is obtained within about 30 minutes, 1 hour, 2 hours, 4 hours, 6 hours, 12 hours, 1 day, 2 days, 3 days, 4 days, 5 days, 1 week, 2 weeks, 3 weeks, 4 weeks, 6 weeks, 8 weeks, 10 weeks, 12 weeks, 4 months, six months or longer of commencing therapy.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1

Processing of Blood Samples and Assay Design

Blood samples are collected by phlebotomists using PAXgene® blood RNA tubes, a tube that is prefilled with a solution to immediately stabilize intracellular RNA from blood cells. RNA can be preserved for 3 days at room temperature, 5 days at 4° C. and up to 8 years if frozen.

As the assay is an RNA-based diagnostic tool, RNA can be extracted from collected blood either manually or using a robot (e.g. Qiacube® from Qiagen®) with commercial RNA extraction kits. In traditional assays, with the use of either DNase treatment or column centrifugation, genomic DNA (gDNA) can be digested or removed during the extraction process, although it is difficult to completely remove gDNA. It will be known to those skilled in the art that treatment of SIRS is more effective if rendered quickly, and thus the extra delay in removal of gDNA can cause patient harm, rendering valuable a method which does not require this time-consuming step. Further, it is challenging and time-consuming to design and screen assays that can hybridize to RNA but not gDNA. The listed assays for each of the claimed biomarkers have been designed to cover as many RNA transcripts as possible and have been validated to generate insignificant or no background on NTC (No Template Control). In addition, all claimed assays have been validated to have insignificant or no background on gDNA, with the background generated with gDNA by GPAA1-WN-Y considered insignificant compared to the signal generated on RNA, even when the carry-over of gDNA reaches 100% the amount of RNA. Therefore, using these primers and probes it is possible to skip the gDNA removal step, which not only reduces the cost, but also decreases the total time of the RNA extraction process.

RNA samples extracted from blood are added as a template, and the triplet member combinations are added as TaqMan assays, to a commercially available Master Mix, which includes everything else needed for RNA amplification, e.g. RNA transcriptase, DNA polymerase, $Mg^{2+}$, buffer, etc. Aliquots of mixture of Master mix, TaqMan assays and RNA template are dispensed to wells of PCR plates, and PCR reactions can start using a real-time PCR thermal cycler, e.g. QuantStudio™ 6 Flex Real-Time PCR System (QS6™). In each cycle, with every new amplicon generated, the Reporter attached to the 5' end, and the Quencher attached to the 3' end of the probe, are permanently separated, and when light strikes the reaction a fluorescent signal is produced that can be detected by the instrument. Fluorescent signals are collected at the end of each cycle, up to a total of 40 cycles. The software used by the real-time PCR thermal cycler analyzes the collected fluorescent signal intensities and generates Ct (Cycle Threshold) values for each sample and each biomarker tested (FIG. 1). The higher the RNA levels, the smaller the Ct values.

Not all, but some, housekeeping genes (HK) are uniformly expressed with low variance under any conditions. In this example, we picked and validated one HK gene and used it to normalize the RNA input in each PCR reaction. As mentioned above with respect to the biomarkers, a Ct value ($Ct_{HK}$) was also generated for the selected HK gene (FIG. 1). For each tested biomarker, a normalized Ct value, Delta Ct=$Ct_{Biomarker}$−$Ct_{HK}$, was generated and used for the score calculation, together with the Delta Ct values of other biomarkers, using a custom validated algorithm. In this example, the score was calculated by taking the geometric mean of delta-Ct values for the included targets.

Figure 2:
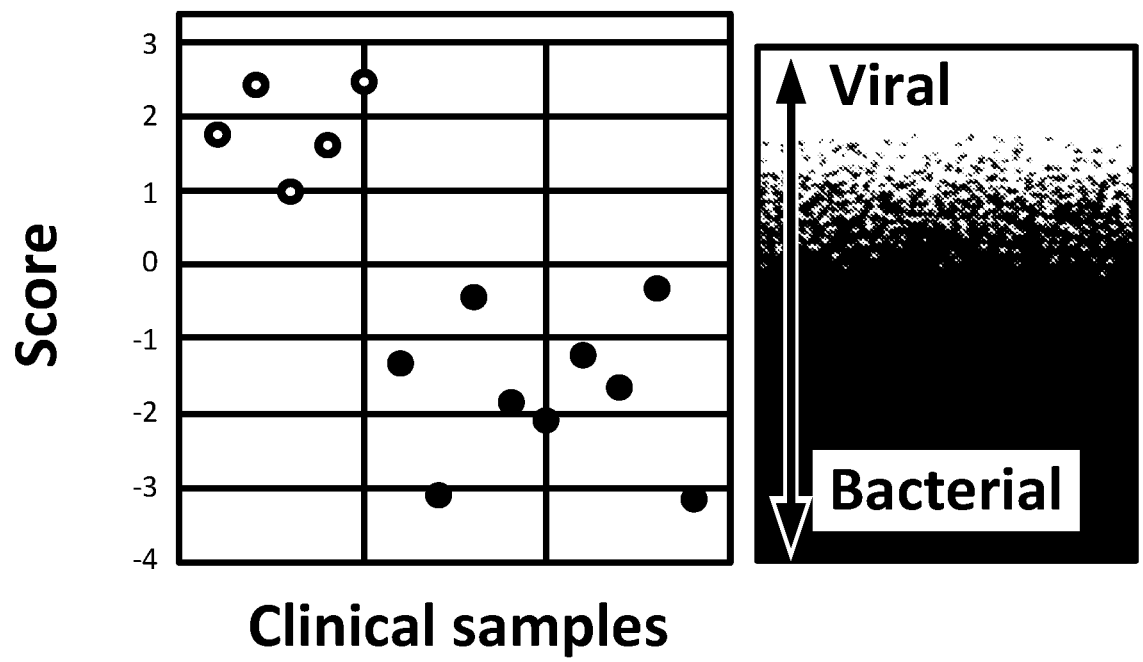
FIG. 2: Calculated scores for each of the 14 tested clinical samples by taking the geometric mean of delta-Ct values of 7 biomarkers (IFI27, HK3, JUP, CTSB, LAX1, GPAA1 and TNIP1). The nine bacterial infected samples (closed circles) are well-separated from the five viral infected samples (open circles), illustrating how the scores calculated using the delta-Ct values can differentiate bacterial from viral infected samples.

The results are shown in FIG. 2, including the calculated scores for each of the 14 tested clinical samples, which were obtained by taking the geometric mean of delta-Ct values of 7 biomarkers (IFI27, HK3, JUP, CTSB, LAX1, GPAA1 and TNIP1). The nine bacterial infected samples (closed circles) are well-separated from the five viral infected samples (open circles), illustrating how the scores calculated using the delta-Ct values can differentiate bacterial from viral infected samples.

```
Sequence Listing
IFI27-B forward primer
                                       SEQ ID NO. 1
AGTCACTGGGAGCAACTG.

IFI27-B probe
                                       SEQ ID NO. 2
ACCAAGTTCATCCTGGGCTCCATT.

IFI27-B reverse primer
                                       SEQ ID NO. 3
CAATGACAGCCGCAATGG.

IFI27-3AA forward primer
                                       SEQ ID NO. 4
AGTGACCAGTGTGGCCAAAGT.

IFI27-3AA probe
                                       SEQ ID NO. 5
CCTCTGGCTCTGCCGTAGTTTTGCC.

IFI27-3AA reverse primer
                                       SEQ ID NO. 6
TCCAATCACAACTGTAGCAATCCT.
```

-continued

| | |
|---|---|
| IFI27-3C forward primer<br>AGTGACCAGTGTGGCCAAAGT. | SEQ ID NO. 7 |
| IFI27-3C probe<br>AGGGGCAAAACTACGGCAGAGCCAG. | SEQ ID NO. 8 |
| IFI27-3C reverse primer<br>TCCAATCACAACTGTAGCAATCCT. | SEQ ID NO. 9 |
| IFI27-3D forward primer<br>AGTGACCAGTGTGGCCAAAGT. | SEQ ID NO. 10 |
| IFI27-3D probe<br>AGGGGCAAAACTACGGCAGAGCCA. | SEQ ID NO. 11 |
| IFI27-3D reverse primer<br>TCCAATCACAACTGTAGCAATCCT. | SEQ ID NO. 12 |
| HK3-A forward primer<br>CCCTCATTTCCTGGACCAAA. | SEQ ID NO. 13 |
| HK3-A probe<br>CTGCTGAGAGATGCCATTCGGAGG. | SEQ ID NO. 14 |
| HK3-A reverse primer<br>AACCACGTCGATGTTGTAGG. | SEQ ID NO. 15 |
| HK3-B forward primer<br>TGCTGAGAGATGCCATTCG. | SEQ ID NO. 16 |
| HK3-B probe<br>ATCGACGTGGTTGCTGTGGTGAA. | SEQ ID NO. 17 |
| HK3-B reverse primer<br>CTACAACTAGCCCAACCTCAC. | SEQ ID NO. 18 |
| HK3-C-NEW forward primer<br>TTTAGGTGCAGTGGTGTGG. | SEQ ID NO. 19 |
| HK3-C-NEW probe<br>CCTCCGAATGGCATCTCTCAGCAG. | SEQ ID NO. 20 |
| HK3-C-NEW reverse primer<br>GTGCCCACTGTGTCGTT. | SEQ ID NO. 21 |
| TNIP1-A forward primer<br>TCCAAGGTGCACAAGAATGA. | SEQ ID NO. 22 |
| TNIP1-A probe<br>ATTCTGCAGACCCTGTGTGAGCAG. | SEQ ID NO. 23 |
| TNIP1-A reverse primer<br>TCAGAGCCTCGTTCTCCTT. | SEQ ID NO. 24 |
| TNIP1-C forward primer<br>TCCAAGGTGCACAAGAATGA. | SEQ ID NO. 25 |
| TNIP1-C probe<br>TGTGAGCAGCTTCGGAAGGAGAAC. | SEQ ID NO. 26 |

-continued

| | |
|---|---|
| TNIP1-C reverse primer<br>ATCCAACTTGGCCTTCAGAG. | SEQ ID NO. 27 |
| LAX1-D forward primer<br>GGAGTATGCGCATTTTCAGTACTG. | SEQ ID NO. 28 |
| LAX1-D probe<br>AGAGCCCGGAGCATGTGCCCTC. | SEQ ID NO. 29 |
| LAX1-D reverse primer<br>GCATGGATGTGGGCTGTATG. | SEQ ID NO. 30 |
| LAX1-E forward primer<br>GGAGTATGCGCATTTTCAGTACTG. | SEQ ID NO. 31 |
| LAX1-E probe<br>CCCGGAGCATGTGCCCTCCC. | SEQ ID NO. 32 |
| LAX1-E reverse primer<br>GCATGGATGTGGGCTGTATG. | SEQ ID NO. 33 |
| LAX1-F forward primer<br>GGAGTATGCGCATTTTCAGTACTG. | SEQ ID NO. 34 |
| LAX1-F probe<br>CCGGAGCATGTGCCCTCCCA. | SEQ ID NO. 35 |
| LAX1-F reverse primer<br>GCATGGATGTGGGCTGTATG. | SEQ ID NO. 36 |
| LAX1-G forward primer<br>GGAGTATGCGCATTTTCAGTACTG. | SEQ ID NO. 37 |
| LAX1-G probe<br>AGCATGTGCCCTCCCAAGCAGG. | SEQ ID NO. 38 |
| LAX1-G reverse primer<br>GCATGGATGTGGGCTGTATG. | SEQ ID NO. 39 |
| GPAA1-WN-Y forward primer<br>TCCTGGTCCTTGGTCTCAA. | SEQ ID NO. 40 |
| GPAA1-WN-Y probe<br>CTGCATCCACAGTTCCAGAGCCT. | SEQ ID NO. 41 |
| GPAA1-WN-Y reverse primer<br>TGATGGGGGAAGGGGTAC. | SEQ ID NO. 42 |
| CTSB-B forward primer<br>ACTTCTACAACGTGGACATGAG. | SEQ ID NO. 43 |
| CTSB-B probe<br>AGGCTATGTGGTACCTTCCTGGGT. | SEQ ID NO. 44 |
| CTSB-B reverse primer<br>GGTCCTCGGTAAACATAACTCTC. | SEQ ID NO. 45 |

What is claimed is:

1. A method of treating systemic inflammatory response syndrome (SIRS), comprising the steps of:
   a. selecting a patient presenting clinical symptoms of systemic inflammatory response syndrome [SIRS] and having a biomarker gene score exceeding a threshold value indicating the presence of a bacterial or a viral infection in the patient, wherein the biomarker gene score is based on the measured expression levels in blood from the patient of at least two biomarker genes selected from the group consisting of IFI27, GPAA1, HK3, TNIP1, and LAX1;
      (i) wherein the expression levels of the biomarker genes are quantitatively determined by amplification and detection of a subsequence of mRNA encoding the biomarker genes,
      (ii) wherein the amplification and detection arises from a use of amplification primer pairs in the presence of undigested genomic DNA and fluorescent probes that bind to the amplified biomarker gene subsequences, and
      (iii) wherein the primer pairs and probes used to amplify the biomarker genes are selected from the group of primer and probe triplet member combinations consisting of:
   Triplet IFI27-B: AGTCACTGGGAGCAACTG (forward primer; SEQ ID NO: 1), ACCAAGTTCATCCTGGGCTCCATT (probe; SEQ ID NO: 2), and CAATGACAGCCGCAATGG (reverse primer; SEQ ID NO: 3);
   Triplet IFI127-3AA: AGTGACCAGTGTGGCCAAAGT (forward primer; SEQ ID NO: 4), CCTCTGGCTCTGCCGTAGTTTTGCC (probe; SEQ ID NO: 5), and TCCAATCACAACTGTAGCAATCCT (reverse primer; SEQ ID NO: 6);
   Triplet IFI27-3C: AGTGACCAGTGTGGCCAAAGT (forward primer; SEQ ID NO: 7), AGGGGCAAAACTACGGCAGAGCCAG (probe; SEQ ID NO: 8), and TCCAATCACAACTGTAGCAATCCT (reverse primer; SEQ ID NO: 9);
   Triplet IFI27-3D: AGTGACCAGTGTGGCCAAAGT (forward primer; SEQ ID NO: 10), AGGGGCAAAACTACGGCAGAGCCA (probe; SEQ ID NO: 11), and TCCAATCACAACTGTAGCAATCCT (reverse primer; SEQ ID NO: 12);
   Triplet HK3-A: CCCTCATTTCCTGGACCAAA (forward primer; SEQ ID NO: 13), CTGCTGAGAGATGCCATTCGGAGG (probe; SEQ ID NO: 14), and AACCACGTCGATGTTGTAGG (reverse primer; SEQ ID NO: 15);
   Triplet HK3-B: TGCTGAGAGATGCCATTCG (forward primer; SEQ ID NO: 16), ATCGACGTGGTTGCTGTGGTGAA (probe; SEQ ID NO: 17), and CTACAACTAGCCCAACCTCAC (reverse primer; SEQ ID NO: 18);
   Triplet HK3-C-NEW: TTTAGGTGCAGTGGTGTGG (forward primer; SEQ ID NO: 19), CCTCCGAATGGCATCTCTCAGCAG (probe; SEQ ID NO: 20), and GTGCCCACTGTGTCGTT (reverse primer; SEQ ID NO: 21);
   Triplet TNIP1-A: TCCAAGGTGCACAAGAATGA (forward primer; SEQ ID NO: 22), ATTCTGCAGACCCTGTGTGAGCAG (probe; SEQ ID NO: 23), and TCAGAGCCTCGTTCTCCTT (reverse primer; SEQ ID NO: 24);

Triplet TNIP-C: TCCAAGGTGCACAAGAATGA (forward primer; SEQ ID NO: 25), TGTGAGCAGCTTCGGAAGGAGAAC (probe; SEQ ID NO: 26), and ATCCAACTTGGCCTTCAGAG (reverse primer; SEQ ID NO: 27);

Triplet LAX1-D: GGAGTATGCGCATTTTCAGTACTG (forward primer; SEQ ID NO: 28), AGAGCCCGGAGCATGTGCCCTC (probe; SEQ ID NO: 29), and GCATGGATGTGGGCTGTATG (reverse primer; SEQ ID NO: 30);

Triplet LAX1-E: GGAGTATGCGCATTTTCAGTACTG (forward primer; SEQ ID NO: 31), CCCGGAGCATGTGCCCTCCC (probe; SEQ ID NO: 32), and GCATGGATGTGGGCTGTATG (reverse primer; SEQ ID NO: 33);

Triplet LAX1-F: GGAGTATGCGCATTTTCAGTACTG (forward primer; SEQ ID NO: 34), CCGGAGCATGTGCCCTCCCA (probe; SEQ ID NO: 35), and GCATGGATGTGGGCTGTATG (reverse primer; SEQ ID NO: 36);

Triplet LAX1-G: GGAGTATGCGCATTTTCAGTACTG (forward primer; SEQ ID NO: 37), AGCATGTGCCCTCCCAAGCAGG (SEQ ID NO: 38), and GCATGGATGTGGGCTGTATG (SEQ ID NO: 39);

Triplet GPAA1-WN-Y: TCCTGGTCCTTGGTCTCAA (forward primer; SEQ ID NO: 40), CTGCATCCACAGTTCCAGAGCCT (probe; SEQ ID NO: 41), and TGATGGGGGAAGGGGTAC (reverse primer; SEQ ID NO: 42); and variants of the primer and probe triplet member combinations listed above, wherein the variants comprise one or more primers or probes comprising one nucleotide substitution relative to any one of SEQ ID NOS:1-42, and wherein the one or more primers or probes comprised by the variants have a GC content of between 45 and 65%; and, b. treating the selected patient with an antimicrobial agent in an amount sufficient to reduce the clinical symptoms of SIRS.

2. The method of claim 1, wherein the antimicrobial agent is an antiviral agent.

3. The method of claim 1, wherein the antimicrobial agent is an antibacterial agent.

4. The method of claim 1, wherein one of the biomarker genes is GPAA1 or IF127.

5. The method of claim 1, wherein the score is further based on an expression level of the biomarker gene CTSB, wherein the CTSB biomarker gene is detected by a combination of three DNA sequences consisting of a forward primer, a reverse primer, and a fluorescent probe having the sequences:

Triplet CTSB-B: ACTTCTACAACGTGGACATGAG (forward primer; SEQ ID NO:43), AGGCTATGTGGTACCTTCCTGGGT (probe; SEQ ID NO:44), and GGTCCTCGGTAAACATAACTCTC (reverse primer; SEQ ID NO:45).

6. The method of claim 1, wherein the probes are labeled with a fluorophore having a maximum fluorescent emission of between 400 and 600 nm.

7. A genetic amplification system for diagnosing systemic inflammatory response syndrome [SIRS], comprising a multiplicity of reaction vessels and a blood sample from a patient presenting clinical symptoms of SIRS, wherein the system is configured to measure expression levels of at least two biomarker genes by amplification and detection of a subsequence of mRNA encoding the biomarker genes, wherein a score generated from the measured expression levels is indicative of a likelihood of the presence of a bacterial or a viral infection in the patient, wherein the biomarker genes are selected from the group consisting of IFI27, GPAA1, HK3, TNIP1, and LAX1, wherein the reaction vessels comprise primer pairs for amplifying the biomarker genes in the presence of undigested genomic DNA and fluorescent probes that bind to the amplified biomarker gene subsequences, and wherein the primer pairs and probes are selected from the group of primer and probe triplet member combinations consisting of:

Triplet IFI27-B: AGTCACTGGGAGCAACTG (forward primer; SEQ ID NO: 1), ACCAAGTTCATCCTGGGCTCCATT (probe; SEQ ID NO: 2), and CAATGACAGCCGCAATGG (reverse primer; SEQ ID NO: 3);

Triplet IFI127-3AA: AGTGACCAGTGTGGCCAAAGT (forward primer; SEQ ID NO: 4), CCTCTGGCTCTGCCGTAGTTTTGCC (probe; SEQ ID NO: 5), and TCCAATCACAACTGTAGCAATCCT (reverse primer; SEQ ID NO: 6);

Triplet IFI27-3C: AGTGACCAGTGTGGCCAAAGT (forward primer; SEQ ID NO: 7), AGGGGCAAAACTACGGCAGAGCCAG (probe; SEQ ID NO: 8), and TCCAATCACAACTGTAGCAATCCT (reverse primer; SEQ ID NO: 9);

Triplet IFI27-3D: AGTGACCAGTGTGGCCAAAGT (forward primer; SEQ ID NO: 10), AGGGGCAAAACTACGGCAGAGCCA (probe; SEQ ID NO: 11), and TCCAATCACAACTGTAGCAATCCT (reverse primer; SEQ ID NO: 12);

Triplet HK3-A: CCCTCATTTCCTGGACCAAA (forward primer; SEQ ID NO: 13), CTGCTGAGAGATGCCATTCGGAGG (probe; SEQ ID NO: 14), and AACCACGTCGATGTTGTAGG (reverse primer; SEQ ID NO: 15);

Triplet HK3-B: TGCTGAGAGATGCCATTCG (forward primer; SEQ ID NO: 16), ATCGACGTGGTTGCTGTGGTGAA (probe; SEQ ID NO: 17), and CTACAACTAGCCCAACCTCAC (reverse primer; SEQ ID NO: 18);

Triplet HK3-C-NEW: TTTAGGTGCAGTGGTGTGG (forward primer; SEQ ID NO: 19), CCTCCGAATGGCATCTCTCAGCAG (probe; SEQ ID NO: 20), and GTGCCCACTGTGTCGTT (reverse primer; SEQ ID NO: 21);

Triplet TNIP1-A: TCCAAGGTGCACAAGAATGA (forward primer; SEQ ID NO: 22), ATTCTGCAGACCCTGTGTGAGCAG (probe; SEQ ID NO: 23), and TCAGAGCCTCGTTCTCCTT (reverse primer; SEQ ID NO: 24);

Triplet TNIP-C: TCCAAGGTGCACAAGAATGA (forward primer; SEQ ID NO: 25), TGTGAGCAGCTTCGGAAGGAGAAC (probe; SEQ ID NO: 26), and ATCCAACTTGGCCTTCAGAG (reverse primer; SEQ ID NO: 27);

Triplet LAX1-D: GGAGTATGCGCATTTTCAGTACTG (forward primer; SEQ ID NO: 28), AGAGCCCGGAG- CATGTGCCCTC (probe; SEQ ID NO: 29), and GCATGGATGTGGGCTGTATG (reverse primer; SEQ ID NO: 30);

Triplet LAX1-E: GGAGTATGCGCATTTTCAGTACTG (forward primer; SEQ ID NO: 31), CCCGGAG-CATGTGCCCTCCC (probe; SEQ ID NO: 32), and GCATGGATGTGGGCTGTATG (reverse primer; SEQ ID NO: 33);

Triplet LAX1-F: GGAGTATGCGCATTTTCAGTACTG (forward primer; SEQ ID NO: 34), CCGGAG-CATGTGCCCTCCCA (probe; SEQ ID NO: 35), and GCATGGATGTGGGCTGTATG (reverse primer; SEQ ID NO: 36);

Triplet LAX1-G: GGAGTATGCGCATTTTCAGTACTG (forward primer; SEQ ID NO: 37), AGCATGTGCCCTCCCAAGCAGG (SEQ ID NO: 38), and GCATGGATGTGGGCTGTATG (SEQ ID NO: 39);

Triplet GPAA1-WN-Y: TCCTGGTCCTTGGTCTCAA (forward primer; SEQ ID NO: 40), CTGCATC-CACAGTTCCAGAGCCT (probe; SEQ ID NO: 41), and TGATGGGGGAAGGGGTAC (reverse primer; SEQ ID NO: 42); and variants of the primer and probe triplet member combinations listed above, wherein the variants comprise one or more primers or probes comprising one nucleotide substitution relative to any one of SEQ ID NOS:1-42, and wherein the one or more primers or probes comprised by the variants have a GC content of between 45 and 65%.

8. The system of claim 7, wherein the reaction vessels are in a thermocycling device designed to heat and cool the vessels.

9. The system of claim 7, wherein one of the biomarker genes is GPAA1 or IFI27.

10. The system of claim 7, wherein the system is further configured to detect a level of the CTSB biomarker gene in the patient, and wherein the CTSB biomarker gene is detected by a combination of three DNA sequences consisting of a forward primer, a reverse primer, and a fluorescent probe having the sequences:

Triplet CTSB-B: ACTTCTACAACGTGGACATGAG (forward primer; SEQ ID NO:43), AGGC-TATGTGGTACCTTCCTGGGT (probe; SEQ ID NO:44), and GGTCCTCGGTAAACATAACTCTC (reverse primer; SEQ ID NO:45).

11. The system of claim 7, wherein the probes are labeled with a fluorophore having a maximum fluorescent emission of between 400 and 600 nm.

12. The system of claim 7, wherein two of the biomarker genes are amplified in the same reaction vessel.

13. A method of diagnosing a bacterial or viral infection in a patient with systemic inflammatory response syndrome [SIRS], comprising:

selecting a blood sample from a patient presenting clinical symptoms of systemic inflammatory response syndrome [SIRS], and quantitatively determining a diagnostic score indicative of a bacterial or viral infection based on measured levels in the patient sample of at least two biomarker genes selected from the group consisting of IFI27, GPAA1, HK3, TNIP1, and LAX1;
(i) wherein the levels of the biomarker genes are measured by amplification and detection of a subsequence of mRNA encoding the biomarker genes and wherein the diagnostic score exceeds a threshold indicative of a bacterial or a viral infection, wherein the threshold value is generated by a quantitative comparison of biomarker gene expression level scores of at least 100 patients known to have a diagnosis of SIRS as well as a bacterial or a viral infection, and 100 healthy controls;
(ii) wherein the amplification and detection arises from the use of amplification primer pairs in the presence of undigested genomic DNA and fluorescent probes that bind to the amplified biomarker gene subsequence, and
(iii) wherein the primer pairs and probes used to amplify the biomarker genes are selected from the group of primer and probe triplet member combinations consisting of:

Triplet IFI27-B: AGTCACTGGGAGCAACTG (forward primer; SEQ ID NO: 1), ACCAAGTT-CATCCTGGGCTCCATT (probe; SEQ ID NO: 2), and CAATGACAGCCGCAATGG (reverse primer; SEQ ID NO: 3);

Triplet IFI127-3AA: AGTGACCAGTGTGGCCAAAGT (forward primer; SEQ ID NO: 4), CCTCTGGCTCTGCCGTAGTTTTGCC (probe; SEQ ID NO: 5), and TCCAAT-CACAACTGTAGCAATCCT (reverse primer; SEQ ID NO: 6);

Triplet IFI27-3C: AGTGACCAGTGTGGCCAAAGT (forward primer; SEQ ID NO: 7), AGGGGCAAAAC-TACGGCAGAGCCAG (probe; SEQ ID NO: 8), and TCCAATCACAACTGTAGCAATCCT (reverse primer; SEQ ID NO: 9);

Triplet IFI27-3D: AGTGACCAGTGTGGCCAAAGT (forward primer; SEQ ID NO: 10), AGGGGCAAAAC-TACGGCAGAGCCA (probe; SEQ ID NO: 11), and TCCAATCACAACTGTAGCAATCCT (reverse primer; SEQ ID NO: 12);

Triplet HK3-A: CCCTCATTTCCTGGACCAAA (forward primer; SEQ ID NO: 13), CTGCT-GAGAGATGCCATTCGGAGG (probe; SEQ ID NO: 14), and AACCACGTCGATGTTGTAGG (reverse primer; SEQ ID NO: 15);

Triplet HK3-B: TGCTGAGAGATGCCATTCG (forward primer; SEQ ID NO: 16), ATCGACGTGGTTGCTGTGGTGAA (probe; SEQ ID NO: 17), and CTACAACTAGCCCAACCTCAC (reverse primer; SEQ ID NO: 18);

Triplet HK3-C-NEW: TTTAGGTGCAGTGGTGTGG (forward primer; SEQ ID NO: 19), CCTCCGAATGG-CATCTCTCAGCAG (probe; SEQ ID NO: 20), and GTGCCCACTGTGTCGTT (reverse primer; SEQ ID NO: 21);

Triplet TNIP1-A: TCCAAGGTGCACAAGAATGA (forward primer; SEQ ID NO: 22), ATTCTGCA-GACCCTGTGTGAGCAG (probe; SEQ ID NO: 23), and TCAGAGCCTCGTTCTCCTT (reverse primer; SEQ ID NO: 24);

Triplet TNIP-C: TCCAAGGTGCACAAGAATGA (forward primer; SEQ ID NO: 25), TGT-GAGCAGCTTCGGAAGGAGAAC (probe; SEQ ID NO: 26), and ATCCAACTTGGCCTTCAGAG (reverse primer; SEQ ID NO: 27);

Triplet LAX1-D: GGAGTATGCGCATTTTCAGTACTG (forward primer; SEQ ID NO: 28), AGAGCCCGGAG-CATGTGCCCTC (probe; SEQ ID NO: 29), and GCATGGATGTGGGCTGTATG (reverse primer; SEQ ID NO: 30);

Triplet LAX1-E: GGAGTATGCGCATTTTCAGTACTG (forward primer; SEQ ID NO: 31), CCCGGAG- CATGTGCCCTCCC (probe; SEQ ID NO: 32), and GCATGGATGTGGGCTGTATG (reverse primer; SEQ ID NO: 33);

Triplet LAX1-F: GGAGTATGCGCATTTTCAGTACTG (forward primer; SEQ ID NO: 34), CCGGAGCATGTGCCCTCCCA (probe; SEQ ID NO: 35), and GCATGGATGTGGGCTGTATG (reverse primer; SEQ ID NO: 36);

Triplet LAX1-G: GGAGTATGCGCATTTTCAGTACTG (forward primer; SEQ ID NO: 37), AGCATGTGCCCTCCCAAGCAGG (SEQ ID NO: 38), and GCATGGATGTGGGCTGTATG (SEQ ID NO: 39);

Triplet GPAA1-WN-Y: TCCTGGTCCTTGGTCTCAA (forward primer; SEQ ID NO: 40), CTGCATCCACAGTTCCAGAGCCT (probe; SEQ ID NO: 41), and TGATGGGGGAAGGGGTAC (reverse primer; SEQ ID NO: 42); and variants of the primer and probe triplet member combinations listed above, wherein the variants comprise one or more primers or probes comprising one nucleotide substitution relative to any one of SEQ ID NOS:1-42, and wherein the one or more primers or probes comprised by the variants have a GC content of between 45 and 65%.

14. The method of claim 13, wherein one of the biomarker genes is GPAA1 or IFI27.

15. The method of claim 13, wherein the probes are labeled with a fluorophore having a maximum fluorescent emission of between 400 and 600 nm.

16. The method of claim 13, wherein the score is further based on an expression level of the biomarker gene CTSB, and wherein the CTSB biomarker gene is detected by a combination of three DNA sequences consisting of a forward primer, a reverse primer, and a fluorescent probe having the sequences:

Triplet CTSB-B: ACTTCTACAACGTGGACATGAG (forward primer; SEQ ID NO:43), AGGCTATGTGGTACCTTCCTGGGT (probe; SEQ ID NO:44), and GGTCCTCGGTAAACATAACTCTC (reverse primer; SEQ ID NO:45).

* * * * *